US010561736B1

(12) United States Patent
Herrero et al.

(10) Patent No.: US 10,561,736 B1
(45) Date of Patent: Feb. 18, 2020

(54) APOPTOSIS INHIBITOR FORMULATIONS FOR PREVENTION OF HEARING LOSS

(71) Applicant: Spiral Therapeutics, Inc., San Francisco, CA (US)

(72) Inventors: Carmen Herrero, Barcelona (ES); Andrew Ayoob, San Francisco, CA (US); Justin Hanes, Baltimore, MD (US); Hugo Peris, San Francisco, CA (US)

(73) Assignee: Spiral Therapeutics, Inc., San Francisco, CA (US)

( * ) Notice: Subject to any disclaimer, the term of this patent is extended or adjusted under 35 U.S.C. 154(b) by 0 days.

(21) Appl. No.: 16/243,892

(22) Filed: Jan. 9, 2019

(51) Int. Cl.
| | |
|---|---|
| *A61K 31/497* | (2006.01) |
| *A61K 31/4965* | (2006.01) |
| *A61K 9/64* | (2006.01) |
| *A61K 47/34* | (2017.01) |
| *A61K 9/00* | (2006.01) |
| *A61K 31/496* | (2006.01) |
| *A61K 9/08* | (2006.01) |
| *A61P 27/16* | (2006.01) |

(52) U.S. Cl.
CPC ............ *A61K 47/34* (2013.01); *A61K 9/0019* (2013.01); *A61K 9/0046* (2013.01); *A61K 9/08* (2013.01); *A61K 31/496* (2013.01); *A61P 27/16* (2018.01)

(58) Field of Classification Search
CPC .................................................... A61K 31/496
USPC ........................ 514/254.09, 255.02, 252.13
See application file for complete search history.

(56) References Cited

U.S. PATENT DOCUMENTS

| | | |
|---|---|---|
| 3,560,503 A | 2/1971 | Anand |
| 5,281,585 A | 1/1994 | Duggan |
| 7,220,431 B2 | 5/2007 | Sawchuk |
| (Continued) | | |

FOREIGN PATENT DOCUMENTS

| | | |
|---|---|---|
| EP | 2296632 | 3/2011 |
| EP | 2460798 | 6/2012 |
| (Continued) | | |

OTHER PUBLICATIONS

Blakley, et al., "Risk factors for ototoxicity due to cisplatin," Arch Otolaryngol Head Neck Surg., 120(5):541-546 (1994).

(Continued)

*Primary Examiner* — Shengjun Wang
(74) *Attorney, Agent, or Firm* — Pabst Patent Group LLP

(57) ABSTRACT

A formulation for sustained release of an apoptosis inhibitor in the inner ear to protect from hearing loss, especially due to exposure to chemotherapy with drugs such as cisplatin. The formulation can be injected through a small gauge needle into the inner ear, where it gels to form a sustained release depot for controlled delivery of drug over a few days. In the preferred embodiment, the formulation includes a thermoresponsive sol-gel polymer such as POLOXAMER 407 and an apoptosis inhibitory agent, preferably an inhibitor of apoptotic protease activating factor-1 (APAF-1), in an effective amount to prevent hearing loss, for example, due to the administration of platinum-based chemotherapeutic agents. As demonstrated by the examples, the hydrogel provides sustained release of an apoptosis inhibitory agent, LPT99, an anti-apoptosis agent that inhibits apoptotic protease activating factor-1 (APAF-1), as well as safety and efficacy in in vitro and in vivo models.

22 Claims, 7 Drawing Sheets

(56) References Cited

U.S. PATENT DOCUMENTS

| | | | |
|---|---|---|---|
| 7,410,944 | B1 | 8/2008 | Shattuck |
| 8,268,866 | B2 | 9/2012 | Guitton |
| 8,318,817 | B2 | 11/2012 | Lichter |
| 8,349,353 | B2 | 1/2013 | Lichter |
| 8,399,018 | B2 | 3/2013 | Lichter |
| 8,507,525 | B2 | 8/2013 | Guitton |
| 8,648,119 | B2 | 2/2014 | Lichter |
| 8,734,836 | B2 | 5/2014 | Sawchuk |
| 8,771,746 | B2 | 7/2014 | Schloss |
| 8,784,870 | B2 | 7/2014 | Lichter |
| 8,828,980 | B2 | 9/2014 | Lichter |
| 8,846,770 | B2 | 9/2014 | Lichter |
| 8,852,626 | B2 | 10/2014 | Lichter |
| 9,066,855 | B2 | 6/2015 | Lichter |
| 9,066,865 | B2 | 6/2015 | Meyer |
| 9,132,087 | B2 | 9/2015 | Lichter |
| 9,205,048 | B2 | 12/2015 | Lichter |
| 9,220,796 | B1 | 12/2015 | Coleman |
| 9,233,068 | B2 | 1/2016 | Lichter |
| 9,326,953 | B2 | 5/2016 | Kester |
| 9,333,171 | B2 | 5/2016 | Lichter |
| 9,427,472 | B2 | 8/2016 | Lichter |
| 9,484,401 | B2 | 11/2016 | Ok |
| 9,486,405 | B2 | 11/2016 | Piu |
| 9,511,020 | B2 | 12/2016 | Lichter |
| 9,603,796 | B2 | 3/2017 | Lichter |
| 9,744,126 | B2 | 8/2017 | Lichter |
| 9,808,460 | B2 | 11/2017 | Lichter |
| 9,867,778 | B2 | 1/2018 | Lichter |
| 10,066,229 | B2 | 9/2018 | Saragovi |
| 10,092,580 | B2 | 10/2018 | Lichter |
| 2010/0016218 | A1 | 1/2010 | Lichter |
| 2010/0016450 | A1 | 1/2010 | Lichter |
| 2012/0122868 | A1 | 5/2012 | Messeguer Pyepoch |
| 2012/0277199 | A1 | 11/2012 | Ye |
| 2013/0045957 | A1 | 2/2013 | Piu |
| 2014/0216439 | A1 | 8/2014 | Soohoo |
| 2014/0348787 | A1 | 11/2014 | Simmons |
| 2015/0306178 | A1 | 10/2015 | Meyer |
| 2015/0374779 | A1 | 12/2015 | Meyer |
| 2016/0199446 | A1 | 7/2016 | Lichter |
| 2016/0228357 | A1 | 8/2016 | Lichter |
| 2017/0029511 | A1 | 2/2017 | Saragovi |
| 2018/0000950 | A1 | 1/2018 | Savel |
| 2018/0085304 | A1 | 3/2018 | Lebel |
| 2018/0092911 | A1 | 4/2018 | Lebel |
| 2019/0000839 | A1 | 1/2019 | Coleman |

FOREIGN PATENT DOCUMENTS

| | | |
|---|---|---|
| WO | 1996000391 | 1/1996 |
| WO | 2007060524 | 5/2007 |
| WO | 2011012746 | 2/2011 |
| WO | 2016004213 | 1/2016 |

OTHER PUBLICATIONS

Campbell, et al., "The effect of D-methionine on cochlear oxidative state with and without cisplatin administration: mechanisms of otoprotection," J. Am. Acad. Audiol.,14(3):144-156 (2003).

Cecconi, et al., "Apaf1 (CED-4 homolog) regulates programmed cell death in mammalian development," Cell, 94(6):727-37 (1998).

Cervantes, et al., "Inhibition of APAF-1 with LPT99 prevents cisplatin-induced apoptosis in HEI-OC1 auditory cells," IEB Symposium, Montpellier, Abstract P77, 188, (2016).

Chen, et al., "In vivo Distribution and Pharmacokinetics of Dexamethasone Sodium Phosphate Thermosensitive in situ Gel Following Intratympanic Injection," 37(3): 456-459 (2006).

Cho, et al., "Release of ciprofloxacin from poloxamer-graft-hyaluronic acid hydrogels in vitro," International Journal of Pharmaceutics, 260:83-91 (2003).

Davis, "Signal transduction by the JNK group of MAP kinases," Cell, 103(2):239-252 (2000).

Escobar-Chavez, et al., "Applications of thermo-reversible pluronic F-127 gels in pharmaceutical formulations," J Pharm Pharm Sci., 9(3):339-358 (2006).

Jeong, et al., "Thermosensitive sol-gel reversible hydrogels," Advanced Drug Delivery Reviews, 54:37-51 (2002).

Lee, et al., "Mechanisms of apoptosis induced by cisplatin in marginal cells in mouse stria vascularis," J. Otorhionlaryngol Relat Spec, 66(3):111-118 (2004).

Macleod, "Tumor suppressor genes," Curr.Op.in Genet. Dev., 10:81-93 (2000).

Malet, et al., "Small molecule inhibitors of Apaf-1-related caspase-3/-9 activation that control mitochondrial-dependent apoptosis," Cell Death and Differentiation, 13(9):1523-1532 (2006).

Maurillo-Cuesta, et al., "Inhibition of Apaf-1 with LPT99 prevents cisplatin-induced hearing loss", IEB Symposium, Montpellier, Abstract P78, 189 (2016).

McAlpine, et al., "The ototoxic mechanism of cisplatin," Hear Res., 47(3):191-203(1990).

Mukherjea, et al., "Expression of the kidney injury molecule 1 in the rat cochlea and induction by cisplatin," Neuroscience, 139(2):733-740 (2006).

Ohlemiller, et al., "Early elevation of cochlear reactive oxygen species following noise exposure," Audiol Neurootol., 4(5):229-236 (1999).

Ohlemiller, et al., "Targeted deletion of the cytosolic Cu/Zn-superoxide dismutase gene (Sod1) increases susceptibility to noise-induced hearing loss," Audio Neurootol., 4(5):237-246 (1999).

Patani, et al., "Bioisosterism: A Rational Approach in Drug Design,", Chem. Rev., 96:3144-3176 (1996).

Paulson, et al., "A novel controlled local drug delivery system for inner ear disease," Laryngoscope, 118(4):706-711 (2008).

Pawlowska, et al., "Dexamethasone and 1,25-Dihydroxyvitamin D3 Reduce Oxidative Stress-Related DNA Damage in Differentiating Osteoblasts," Int. J. Mol. Sci., 15:16649-16664 (2014).

Ruel-Gariepy, et al., "In situ-forming hydrogels-review of temperature-sensitive systems," European Journal of Pharmaceutics and Biopharmaceutics, 58:409-426 (2004).

Salt, et al., "Local inner-ear drug delivery and pharmacokinetics," Drug Discov Today, 10(19):1299-1306 (2005).

Shah, et al., "Formation of reactive oxygen species following bioactivation of gentamicin," Free Radical Biology and Medicine, 26(3-4):341-347 (1999).

Shin, et al., "Mucoadhesive and physicochemical characterization of Carbopol-Poloxamer gels containing triamcinolone acetonide," Drug Dev Ind Pharm., 26(3):307-312 (2000).

Soengas, et al., "Apaf-1 and caspase-9 in p53-dependent apoptosis and tumor inhibition," Science, 284(5411):156-159 (1999).

Wang, et al., "Dose-dependent sustained release of dexamethasone in inner ear cochlear fluids using a novel local delivery approach," 14(6):393-401 (2009).

Yorgason, et al., "Understanding drug ototoxicity: molecular insights for prevention and clinical management," Expert Opinion on Drug Safety, 5(3):383-399 (2006).

Yoshida, et al., "Apaf1 is required for mitochondrial pathways of apoptosis and brain development," Cell, 94(6):739 750 (1998).

APOPTOSIS INHIBITOR FORMULATIONS FOR PREVENTION OF HEARING LOSS

FIELD OF THE INVENTION

The invention is in the field of formulations for prevention of hearing loss, particularly formulations containing an apoptosis inhibitor in a formulation providing controlled delivery over a period of days for preventing hearing loss associated with exposure to ototoxic agents such as chemotherapeutics, exposure to loud noise, aging, or autoimmune inner ear disease.

BACKGROUND OF THE INVENTION

Hearing loss is one of the most common disorders of the inner ear. According to the Hearing Loss Association of America (HLAA), approximately 48 million individuals, or 20% of the United States (US) population, are affected by hearing loss (hearingloss.org/content/basic-facts-about-hearing-loss). The impact of hearing loss on quality of life can be quite profound. An individual's emotional and mental state may be affected by the disrupted communication patterns caused by hearing loss, which can result in a restricted social life.

Sensorineural hearing loss may occur acutely and irreversibly, due to aging, exposure to loud noise (acoustic trauma) or certain ototoxic agents. Numerous commonly used drugs have been associated with ototoxicity and hearing loss including aminoglycoside antibiotics and other antimicrobials, loop diuretics, salicylates, and platinum-based chemotherapeutic agents (Yorgason, et al., Expert Opinion on Drug Safety 2006, 5(3), 383-399).

Platinum-based chemotherapeutic agents have shown efficacy in the prevention of a variety of malignant neoplasms in adults and children. Three platinum-based chemotherapeutic agents are currently approved in the US: cisplatin (CisPt), carboplatin, and oxaliplatin. Of these three drugs, CisPt is the most widely used to prevent many childhood cancers, alone or in combination with other agents.

In patients suffering drug-induced ototoxicity, substantial variability has been seen in the incidence of hearing loss after prevention with CisPt, based on factors such as the type of cancer being prevented, administered dose, age of the patient, renal function, and other concomitantly administered drugs. However, the incidence and severity of ototoxicity is directly related to the cumulative CisPt dose. With CisPt therapy, the incidence of aminoglycoside-induced ototoxicity is 0.5% to 60%, depending on the type of aminoglycoside administered, cumulative dose, route of administration, and duration of prevention.

Apoptotic loss of cochlear hair cells appears to be one of the main underlying causes of ototoxic hearing loss. Since these cells do not regenerative in humans, uncontrolled hair cell death results in irreversible hearing loss. The trigger for this cell loss is the mass production of reactive oxygen species (ROS) that activate the mitochondrial or intrinsic pathway of apoptosis. Mass production of ROS results in activation of c-Jun N-terminal kinase (JNK) (Davis, Cell 2000, 103(2), 239-252), which is then translocated to the nucleus, where it activates transcription of genes involved in caspase-dependent mitochondrial apoptosis. The role of ROS in ototoxicity has been confirmed by the results obtained with superoxide dismutase (Sod1) or glutathione peroxidase (Gpx1) in knockout mice, which showed increased susceptibility to acoustic trauma-induced hearing loss (Ohlemiller, et al., Audiol. Neurootol. 1999, 4, 229-236 and 237-246 (1999a, 1999b). Conversely, animals that overexpressed Sod1 showed a greater resistance to aminoglycoside-induced ototoxicity (Shah, et al., Free Radical Biology and Medicine 1999, 26(3-4), 341-347).

One of the key events in the process of apoptotic cell death is the formation of a 700 kDa molecular complex called apoptosome. The apoptosome is integrated by cytochrome c (Cytc), procaspase-9 (PC9), and the Apaf-1 protein. The apoptosome's physiological importance in apoptosis was shown in experiments in which mice that were null for the gene APAF-1 (Apaf-/-) exhibited marked embryonic lethality, with major craniofacial defects and brain injury (Cecconi, et al., Cell 1998, 94, 727-37; Yoshida, et al., Cell 1998, 94, 739-750). Both PC9 and Apaf-1 are essential for p53-mediated apoptosis and are presented as tumor suppressor genes (Soengas, et al., Science 1999, 284(5411), 156-9; Macleod, Curr. Op. in Genet. Dev. 2000, 10, 81-93).

CisPt enters the outer hair cells primarily through the ion channels of its apical stereocilia. After CisPt is inside the cell, it forms a highly reactive monohydrate complex that induces transcription of the enzyme, NADPH (nicotinamide adenine dinucleotide phosphate) oxidase 3, resulting in mass production of ROS and therefore activating the intrinsic apoptosis pathway. The nitric oxide synthase (NOX) enzyme induction has been demonstrated in ex vivo experiments in rat cochleae treated with different doses of CisPt (Mukherjea, et al., Neuroscience 2006, 139(2), 8).

Histopathologic studies have shown that these platinum-based chemotherapeutic agents cause progressive destruction of outer hair cells, inner hair cells, and supporting cells within the organ of Corti in the basal region of the cochlea (Blakley, et al., Arch Otolaryngol Head Neck Surg. 120, 541-546), as well as cells within the stria vascularis (Lee, J. E. et al, J. Otorhionlaryngol Relat Spec 66, 111-118). CisPt appears to block transduction channels within the outer hair cells of the cochlea (McAlpine and Johnstone, Hear Res. 1990, 47(3), 191-203), and to be associated with the generation of ROS, depletion of intracellular glutathione, and interference with antioxidant enzymes within the cochlea (Campbell, J. Am. Acad. Audiol. 2003, 14(3), 144-56).

Due to the irreversible nature of sensorineural hearing loss, vestibular impairment, and tinnitus resulting from ototoxic drugs, exposure to loud noise, aging, and autoimmune disease, a significant unmet need exists for preventive therapeutic approaches.

Therefore, it is an object of the invention to provide formulations with beneficial effects that can be administered for sustained local delivery of protective agents, that minimizes risk of systemic exposure.

It is another object of the invention to provide formulations with beneficial effects such as reduction and/or prevention of hearing loss.

It is a further object of the invention to provide formulations beneficial effects such as reduction and/or prevention of hearing loss associated with exposure to ototoxic agents such as chemotherapeutics, exposure to loud noise, aging, infection, or autoimmune inner ear disease.

SUMMARY OF THE INVENTION

A controlled release formulation delivers an apoptosis inhibitory agent, preferably an APAF-1 inhibitor, in an effective amount to prevent hearing loss associated with exposure to ototoxic agents such as chemotherapeutics, exposure to loud noise, aging, autoimmune inner ear disease or a combination thereof. The formulation is particularly effective in preventing otoxicity arising from the administration of platinum-based chemotherapeutic agents.

The formulation for otic delivery is in the form of a solution or suspension that effects a transition from a liquid state at room temperature to a hydrogel at body temperature. Preferred formulations are a solution, not suspension, of a synthetic polymer such as a POLOXAMER®, which are triblock copolymers of poly(ethylene oxide) (PEO) and poly(propylene oxide) (PPO) available in different molecular weights and PPO/PEO ratios. The formulation is administered as a liquid which solidifies into the hydrogel at body temperature, so that the hydrogel provides sustained release of the apoptosis inhibitory agent for a period of between at least three to fifteen days in the ear.

In a preferred embodiment for preventing hearing loss, especially due to chemotherapeutic agents, the apoptosis inhibitory agent is 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide (LPT99), an anti-apoptosis agent that inhibits apoptotic protease activating factor-1 (APAF-1). In a preferred embodiment, the hydrogel forming excipient is POLOXAMER® 407. The amount of the apoptosis inhibitory agent constitutes between about 0.0031% w/w and about 1.5% w/w of the formulation, while the hydrogel forming polymer constitutes between 10% and 30% by weight of the polymer, with the most preferred amount of a polymer such as POLOXAMER® 407 constituting about 15% w/w of the formulation. This is a solution, not a suspension, which is extremely stable at room temperature for a period of at least three months.

Prior to introducing the apoptosis inhibitory agent, the phase-transition hydrogel forming polymer such as POLOXAMER® 407 preferably is formulated as a liquid product including an amount of POLOXAMER® 407 that at body temperature forms a hydrogel providing sustained release of the apoptosis inhibitory agent. The apoptosis inhibitor, preferably LPT99, is added to the formulation to form a homogeneous solution without causing gelation. LPT99 unexpectedly dissolves to a high concentration that increases the diffusive driving force through the round window membrane, and is extremely stable (remaining in solution, without forming precipitate) at room temperature. The formulation has a viscosity suitable for injection through a 23-G needle, typically through the tympanic membrane into the tympanic cavity. The formulation may further include sodium chloride, water, antioxidants, antimicrobials, detergents, solubilizing agents, crystallization inhibitors, viscosity modifiers, chelators, and buffers including, but not limited to, hydrogen phosphate di-sodium dodecahydrate and dihydrogen sodium phosphate dihydrate.

Preferred apoptosis inhibitors such as LPT99 and/or its pharmaceutically acceptable salts are useful for the prophylaxis and/or prevention of a pathological and/or physiological condition associated with an increase of apoptosis by means of its Apaf-1 inhibiting activity such as ototoxicity associated with platinum-based chemotherapeutic agents. Longer term release formulations or a depo or pump can be used to reduce age associated hearing loss.

BRIEF DESCRIPTION OF THE DRAWINGS

FIG. 2A is over a range of 5-25° C.; FIG. 2B is over a range of 5-37° C.

FIG. 3B, %) over days in situ.

Treatments were:
Vehicle cisplatin+VehiclevSPT991 (n=10)
Cisplatin+Vehicle SPT991 (n=9)
Cisplatin+SPT991 300 ug/mL (n=10)
Cisplatin+SPT991-CD (n=10)

Figure 6A:
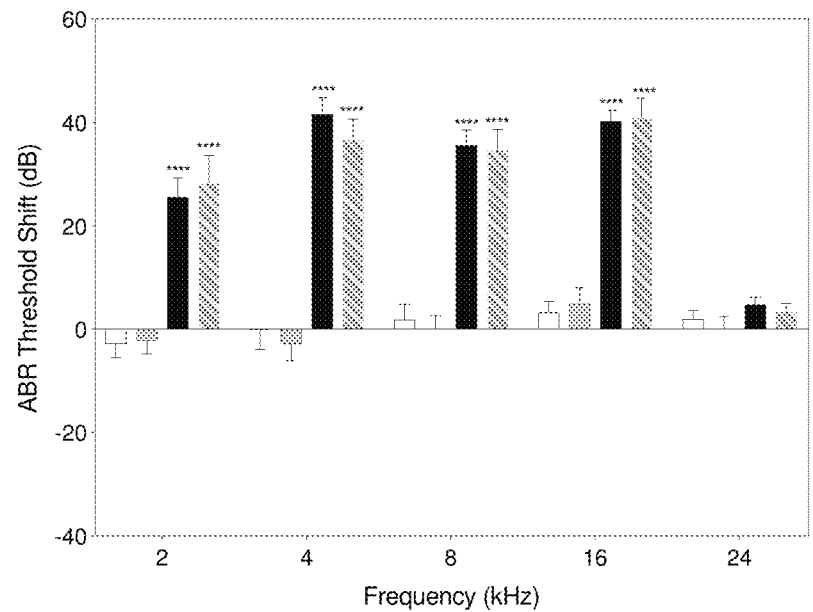
Figure 6B:
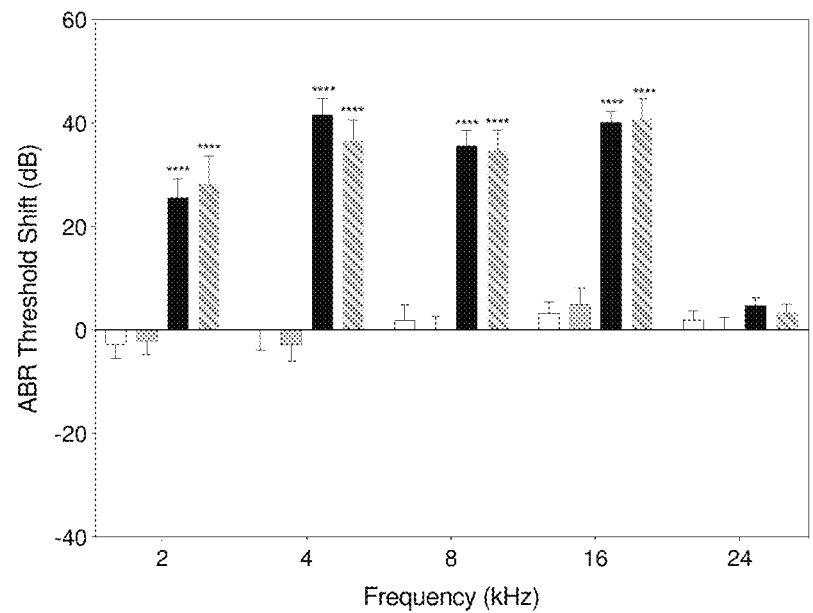
Figure 6C:
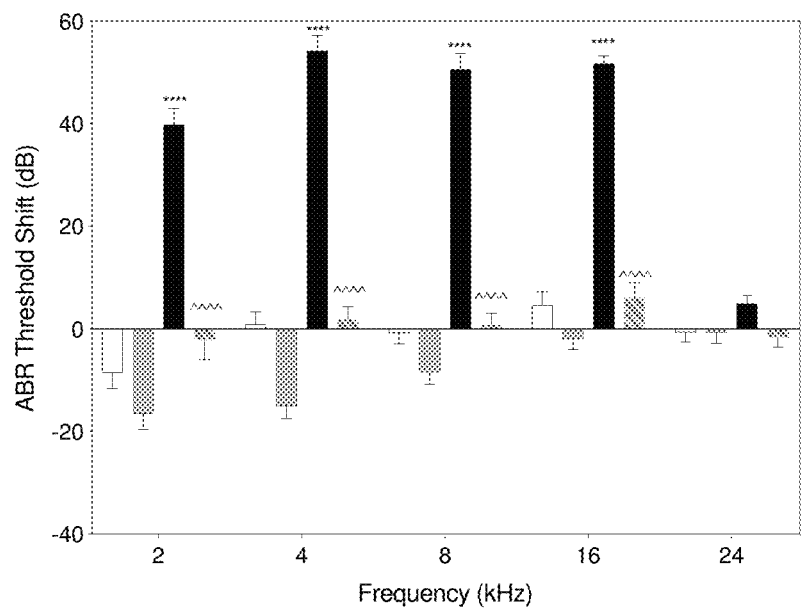

FIGS. 6A, 6B, and 6C are graphs of ABR threshold (dB) versus frequency (kHz) 24 hrs (FIG. 6A), 10 days (FIG. 6B), and 21 days (FIG. 6C) after administration, for:
☐ CONTROL (n=11, 2 ears)
▒ CONTROL+VEHICLE (N=11, 2 ears)
■ TRAUMA (n=15, 2 ears)
▧ TRAUMA+LPT99 (n=15, 2 ears)

The results demonstrate that noise exposure induces an increase in ABR Threshold shift in non-treated groups. Noise-induced ABR Threshold Shift is present at 1, 10 and 21 days in LPT99-treated groups, ABR Threshold shift is back at basal levels at 10 and 21 days.

DETAILED DESCRIPTION OF THE INVENTION

I. Definitions

"Active agent" and "active pharmaceutical ingredient" are used interchangeably and refer to a physiologically or pharmacologically active substance that acts locally and/or systemically in the body. An active agent is a substance that is administered to a patient for the treatment (e.g., apoptotic inhibitory agent), prevention, or diagnosis of a disease or disorder.

The term "adenosine receptor 3" or "A3" or "ADORA3" is a purinergic G-coupled receptor involved in a variety of intracellular signaling pathways.

The term "ADME" is an abbreviation in pharmacokinetics and pharmacology for "absorption, distribution, metabolism, and excretion", and describes the disposition of a pharmaceutical compound within an organism. These four criteria all influence the drug levels and kinetics of drug exposure to the tissues and hence influence the performance and pharmacological activity of the compound as a drug.

The term "Apaf-1" or "apoptotic protease activating factor-1" is a cytoplasmic protein that forms one of the central hubs in the apoptosis regulatory network. Upon binding cytochrome c and dATP, this protein forms an oligomeric apoptosome which binds and cleaves Procaspase 9 protein, releasing its mature, activated form.

The term "apoptosis" means is a process of programmed cell death that occurs in multicellular organisms. Biochemical events lead to characteristic cell changes (morphology) and death. Apoptosis is a highly regulated and controlled process that confers advantages during an organism's lifecycle.

The term "AUC" or "area under the curve" in the field of pharmacokinetics, the area under the curve (AUC) is the definite integral in a plot of drug concentration in blood plasma versus time. In practice, the drug concentration is measured at certain discrete points in time and the trapezoidal rule is used to estimate AUC.

The term "auditory brainstem response" or "ABR" refers to an auditory evoked potential extracted from ongoing electrical activity in the brain and recorded via electrodes placed on, for example, the scalp.

The term "blood labyrinth barrier" or "BLB" refers to the barrier between the vasculature and the inner ear fluids, either endolymph or perilymph. The BLB is critical for the maintenance of the inner ear fluid ionic homeostasis.

The term "BLLQ" is an abbreviation for "below the lower limit of quantification" and is defines as below the lowest standard on the calibration curve.

The term "cholecystokinin receptor 1" or "CCK1" is a G-protein coupled receptor that bines sulfated members of the cholecystokinin family of peptide hormones.

The term "$C_{max}$" refers to the maximum (or peak) concentration that a drug achieves in a specified compartment or test area of the body after the dug has been administered and before the administration of a second dose. It is a standard measurement in pharmacokinetics.

The term "Cmin" refers to the minimum (or trough) concentration that a drug achieves after dosing.

The term "Cytc" or "cyctochrome c" refers to a small hemeprotein found loosely associated with the inner membrane of the mitochondrion. It has an intermediate role in apoptosis in activating caspase 9 via the apoptosome.

The term "cytocochleogram" refers to a graphic representation of the anatomical state of the hair cells along the complete width and length of the organ of Corti.

The term "drug absorption" or "absorption" refers, preferably, to the process of movement of the active agent from the localized site of administration, by way of example only, the round window niche of the cochlea, and across a barrier (the round window membrane, as described below) into the auris interna or inner ear structures.

The abbreviation "DDI" refers to drug-drug interaction.

The terms "effective amount" or "therapeutically effective amount," as used herein, refer to a sufficient amount, preferably, of the otic agent being administered that would be expected to relieve to some extent one or more of the symptoms of the disease or condition being prevented, i.e., a quantity necessary to render the desired apoptotic inhibitory result. The term "therapeutically effective amount" includes, for example, an "effective amount" of an otic agent to achieve a desired pharmacologic effect or apoptotic inhibitory improvement without undue adverse side effects. It is understood that "an effective amount" or "a therapeutically effective amount" varies, in some implementations, from subject to subject, due to variation in metabolism of the compound administered, age, weight, general condition of the subject, the condition being prevented, the severity of the condition being prevented, and the judgment of the prescribing physician. It is also understood that "an effective amount" in an extended-release dosing format may differ from "an effective amount" in an immediate-release dosing format based upon pharmacokinetic and pharmacodynamic considerations.

The term "enhance" or "enhancing," refers to an increase or prolongation of either the potency or duration of a desired effect, preferably, of the otic agent, or a diminution of any adverse symptomatology. For example, in reference to enhancing the effect of the otic agents disclosed herein, the term "enhancing" refers to the ability to increase or prolong, either in potency or duration, the effect of other apoptotic inhibitory agents that are used in combination with the otic agents disclosed herein.

The term "GLP" refers to "good laboratory practice" and is a set of principles intended to assure the quality and integrity of non-clinical laboratory studies.

The term "hERG" refers to human ether-a-go-go-related gene that codes for a protein that is the alpha subunit of a potassium ion channel.

The terms "inhibit" and "reduce" mean to reduce or decrease in activity or expression. The terms also include preventing, slowing, or reversing the development of a condition, for example, ototoxicity, or advancement of a condition in a patient necessitating prevention. This can be a complete inhibition or reduction of activity or expression, or a partial inhibition or reduction. Inhibition or reduction can be compared to a control or to a standard level.

The term "MRSD" or "maximum recommended starting dose" refers to the highest amount of an agent that can be given safely and without complication while maintaining its efficacy.

The term "MTD" or "maximum tolerated dose" refers to the highest dose of a drug or prevention that does not cause unacceptable side effects.

The term "NOAEL" refers to "no observed adverse effect level" and is an important part of the non-clinical risk assessment.

The term "ototoxicity" means the property of being toxic to the ear, specifically the cochlea, including the cochlear sensory hair cells, or auditory nerve and sometimes the vestibular system, for example, as a side effect of a drug. The effects of ototoxicity can be reversible and temporary, or irreversible and permanent. There are many well-known ototoxic drugs used in clinical situations, and they are prescribed, despite the risk of hearing disorders, for treatment of very serious health conditions such as aggressive cancers or bacterial infections. Ototoxic drugs include antibiotics such as gentamicin, loop diuretics such as furosemide and platinum-based chemotherapy agents such as cisplatin. A number of nonsteroidal anti-inflammatory drugs (NSAIDS) have also been shown to be ototoxic. This can result in sensorineural hearing loss, dysequilibrium, or both. Some environmental and occupational chemicals have also been shown to affect the auditory system.

The term "pharmaceutically acceptable salts" means those salts which conserve the efficiency and the biological properties of the free bases or free acids.

The term "auris-acceptable penetration enhancer" or "penetration enhancer" refers to an agent that reduces barrier resistance (e.g., barrier resistance of the round window membrane).

The term "pharmacodynamic" refers to the factors that determine the biologic response observed relative to the concentration of drug at the desired site, such as within the auris media and/or auris interna.

The term "pharmacokinetics" refers to factors that determine the attainment and maintenance of the appropriate concentration of drug at the desired site, such as within the auris media and/or auris interna.

The term "platinum-based antineoplastic drugs" or "platins" are chemotherapeutic agents such as cisplatin, oxaliplatin, and carboplatin, used to kill cancerous cells. They are coordination complexes of platinum. These drugs are used to treat almost half of people receiving chemotherapy for cancer.

The term "prophylactically effective amount or dose" refers to an amount of a composition administered to a patient susceptible to or otherwise at risk of a particular disease, disorder or condition, for example, ototoxicity. For example, the apoptotic inhibitory formulation may be administered to an individual prior to chemotherapy to prevent hearing loss by the subsequently administered chemotherapeutic agent.

The term "room temperature" refers to a temperature between about 15° C. and less than about 27° C., preferably 25° C.

The term "body temperature" refers to a temperature between about 36.5° C. and about 37.5° C., preferably 37° C.

The term "ROS" or "reactive oxygen species" are chemically reactive chemical species containing oxygen.

"Small molecule" generally refers to an organic molecule that is less than about 2000 g/mol in molecular weight, less than about 1500 g/mol, less than about 1000 g/mol, less than about 800 g/mol, or less than about 500 g/mol. In some forms, small molecules are non-polymeric and/or non-oligomeric.

"Steady state," refers to when the amount of drug administered, preferably, to the auris media and/or auris interna is equal to the amount of drug eliminated within one dosing interval resulting in a plateau or constant levels of drug exposure within the targeted structure.

"Stable" as used herein refers to chemical and physical stability over a time period under defined conditions. Physical stability refers to a high percentage or all of what was originally dissolved remaining in solution. In a preferred embodiment this value is greater than 60, 70, 80, 90, or 100% remaining dissolved at room temperature.

"Sustained release" as used herein refers to release of a substance over an extended period of time in contrast to a bolus type administration, in which the entire amount of the substance is made biologically available at one time.

The term "$T_{max}$" refers to the time it takes a drug or other substance to reach the maximum concentration $C_{max}$.

The term "transtympanic administration" refers to the administration of a therapeutic, or agent via the tympanic cavity, preferably via a hypodermal needle that accesses the tympanic cavity (middle ear) by penetrating the tympanic membrane (eardrum).

The terms "prevent," "preventing" or "prevention," as used herein, include alleviating, abating or ameliorating a disease or condition, for example ototoxicity, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or controlling or stopping the symptoms of the disease or condition.

II. Controlled Release Apoptosis Inhibitory Compositions

Auris or otic compositions have been developed for extended release, either continuously or in a pulsatile manner, or variants of both, of an apoptotic agent within the ear. The extended release otic composition increases the area under the curve (AUC) of the agent being delivered in otic fluids (e.g., endolymph and/or perilymph) by about 30%, about 40%, about 50%, about 60%, about 70%, about 80% or about 90% compared to a composition that is not an extended release otic composition. The extended release compositions may also decrease the $C_{m}ax$ in otic fluids (e.g., endolymph and/or perilymph) by about 40%, about 30%, about 20%, or about 10%, compared to a composition that is not an extended release otic composition. This reduces the ratio of $C_{max}$ to $C_{min}$ compared to a composition that is not an extended release otic composition. In certain implementations, the ratio of $C_{max}$ to $C_{min}$ is 10:1, 9:1, 8:1, 7:1, 6:1, 5:1, 4:1, 3:1, 2:1 or 1:1. The length of time that the concentration of an otic agent is above $C_{min}$ by about 30%, about 40%, about 50%, about 60%, about 70%, about 80% or about 90% compared to a composition that is not a extended release otic composition. In certain instances, the extended release compositions delay the time to $C_{max}$, and/or prolongs the time the concentration of the drug will stay above the $C_{min}$. In some forms, auris compositions prolong the residence time of a drug in the inner ear. In the preferred embodiment, once the concentration in the endolymph or perilymph of a drug reaches steady state, the concentration of the drug in the endolymph or perilymph stays at or about the apoptotic inhibitory dose for an extended period of time (e.g., one day, 2 days, 3 days, 4 days, 5 days, 6 days, or 1 week).

The compositions have at least three components: apoptotic inhibitory agent; gel forming polymer; and other excipients, which together form an extended release composition to be administered into the ear.

A. Apoptotic Inhibitory Agents

The formulation can be used for the administration of an apoptotic agent to the inner ear. Preferably, the apoptosis inhibitory agent inhibits a protein in the intrinsic or mitochondrial medial apoptosis pathway, especially, apoptotic protease activating factor-1 (Apaf-1); inhibits apoptosis of hair cells, such as cochlear hair cells from an insult that causes loss of a portion of hair cells; decreases cytochrome c release, or a combination thereof. Hearing loss is often associated with sensory hair cell death induced by exposure to ototoxic agents such as chemotherapeutics, exposure to loud noise, aging, cholesteatoma, autoimmune inner ear disease or a combination thereof. In particular, the associated ototoxicity arises from the administration of chemotherapeutic agents, such as platinum-based chemotherapeutic agents.

The intrinsic or mitochondria mediated apoptosis pathway can be initiated by a number of cellular stress factors that together with the participation of members of the BCL-2 family of proteins, lead to mitochondrial outer membrane permeabilization (MOMP). This is followed by cytochrome c (Cytc) release from mitochondria that binds to the protein Apaf-1 (apoptotic protease-activating factor) and forms the multiprotein complex termed apoptosome. The apoptosome recruits and activates an initiator member of the caspase family of cysteine aspartyl proteases, procaspase-9, that in turn activates apoptosis-effector caspases initiating therefore apoptotic cell death. Defects in the regulation of apoptosis are at the root of a variety of diseases. When cells show low apoptosis it frequently correlates with cancer or autoimmune diseases. In contrast, excessive apoptosis induces unwanted cell death and promotes pathological conditions related to stroke, ischemia-reperfusion damage and degenerative diseases. Therefore, there is a medical need for treatments based on unwanted apoptosis inhibition, but no treatment has been approved. In this sense, drug discovery efforts initially targeted the inhibition of caspase activity, particularly a family of protease enzymes called caspases. This strategy demonstrated a promising potential in several animal models, but may be associated with side effects. Furthermore, caspase inhibition alone may insufficient to curtail apoptosis in animal models and humans.

Caspases (cysteine-aspartic proteases, cysteine aspartases or cysteine-dependent aspartate-directed proteases) are a family of protease enzymes (specifically intracellular cysteine proteases) playing essential roles in programmed cell death (including apoptosis, pyroptosis and necroptosis) and inflammation. Caspase inhibitors may be delivered using the formulations described herein. The small molecule pan-caspase inhibitor VX-166 has garnered interest for its ability to treat fibrosis and sepsis. A number of others have been described.

A number of Apaf-1 inhibitors have been identified, as reported by Mar Orzáez, PLoS One. 2014; 9(10): e110979. See also Wang, et al. Sci. Rep. 2016, 6:29820.

Of special interest are the protein-protein interactions upstream of caspase activation in particular, the formation of the apoptosome offered evidences to be considered as an interesting target for developing anti-apoptotic therapies. The main constituent of the apoptosome is Apaf-1, a protein involved in nucleotide and Cytc binding. Apaf-1 is a multidomain protein with an N-terminal caspase recruitment domain (CARD), a central nucleotide-binding and oligomerization domain (NOD), and a C-terminal WD40 repeats domain.

In some forms, the apoptosis inhibitory agent contains a 1,4-piperazine-2,5-dione moiety or a pharmaceutically acceptable salt thereof. The apoptosis inhibitory agent can be a compound of Formula I, shown below, or a pharmaceutically acceptable salt thereof:

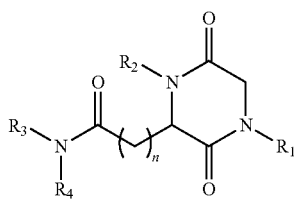

Formula I wherein:

$R_1$ and $R_2$ are independently hydrogen, $C_{1-5}$ alkyl, $C_{2-5}$ alkenyl, $(CH_2)_{0-3}$-cycloalkyl, —$(CH_2)_{1-3}$-heterocycle, —$(CH_2)_{0-3}$-aryl, —$(CH_2)_{0-3}$-heteroaryl, —$(CH_2)_{1-2}$—CH(aryl)$_2$, —$(CH_2)_{1-2}$—CH(aryl)(heteroaryl), or —$(CH_2)_{1-2}$—CH(heteroaryl)$_2$;

$R_3$ is selected from hydrogen, $C_{1-5}$ alkyl, $C_{2-5}$ alkenyl, $(CH_2)_{0-3}$-cycloalkyl, —$(CH_2)_{1-3}$-heterocycle, —$(CH_2)_{1-3}$-aryl, —$(CH_2)_{1-3}$-heteroaryl, —$(CH_2)_{1-3}$—CONR$_5$R$_6$, —$(CH_2)_{1-2}$—CH(aryl)$_2$, —$(CH_2)_{1-2}$—CH(aryl)(heteroaryl), and —$(CH_2)_{1-2}$—CH(heteroaryl)$_2$;

$R_4$ is hydrogen, —$C_{1-5}$ alkyl, —$(CHR_7)_{1-3}$—CO—NR$_5$R$_6$, —$(CHR_7)_{1-3}$—CO—OR$_5$, —$(CH_2)_{1-3}$—NR$_5$R$_6$, —$(CH_2)_{1-3}$—CO[NCHR$_7$CO]$_m$NH$_2$, —$(CH_2)_{1-3}$—CO[NCHR$_7$CO]$_m$OR$_5$;

n is 1 or 2; m is 1, 2, or 3;

$R_5$ and $R_6$ are independently from hydrogen, —$C_{1-5}$ alkyl, or —$(CH_2)_{0-3}$-aryl;

each $R_7$ is independently hydrogen, —$C_{1-5}$ alkyl, —$(CH_2)_{1-3}$-aryl, or —$(CH_2)_{1-3}$-heteroaryl;

wherein the $C_{1-5}$ alkyl, $C_{2-5}$ alkenyl, cycloalkyl and heterocycle groups are optionally substituted with one or more substituents selected independently from halogen, OR$_5$, OCF$_3$, SH, SR$_5$, NR$_5$R$_6$, NHCOR$_5$, COOH, COOR$_5$, OCOR$_5$, aryl, and heteroaryl;

wherein the aryl and heteroaryl groups are optionally substituted with one or more substituents selected independently from halogen, CF3, OR$_5$, OCF$_3$, SH, SR$_5$, NH$_2$, NHCOR$_5$; NO$_2$, CN, COR$_5$, COOR$_5$, OCOR$_5$, CONR$_5$R$_6$, —$(CH_2)_{0-3}$NR$_5$R$_6$, SO$_2$NH$_2$, NHSO$_2$CH$_3$, $C_{1-5}$ alkyl, aryl and heteroaryl;

wherein the heterocycle and heteroaryl groups are optionally substituted on a secondary nitrogen atom with $C_{1-5}$ alkyl, cycloalkyl, or —$(CH_2)_{0-3}$-aryl; and on the condition that (i) when $R_2$ is 2-(4-fluorophenyl)ethyl, $R_4$ is —$CH_2$—CO—NH$_2$ and n is 1; (ii) if $R_1$ is 2-(4-fluorophenyl)ethyl, $R_3$ is not 2-(4-methoxyphenyl)ethyl, 2-(2-pyridyl)ethyl or 2-(2,4-dichlorophenyl)ethyl; and (iii) if $R_1$ is 2-(2,4-dichlorophenyl)ethyl, $R_3$ is not 2-(4-methoxyphenyl)ethyl, or 2-(2-pyridyl)ethyl.

In some forms, the apoptosis inhibitory agent is a compound having the structure:

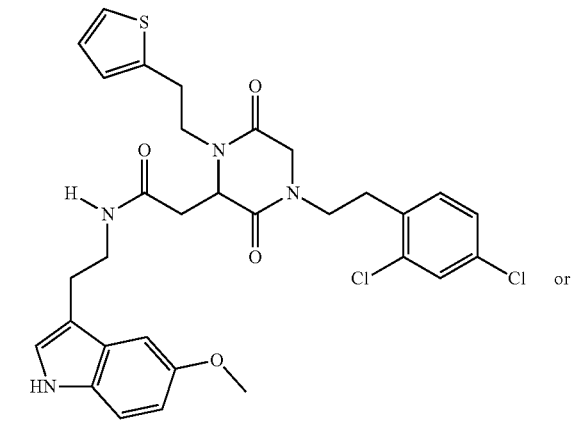

LPT99 or

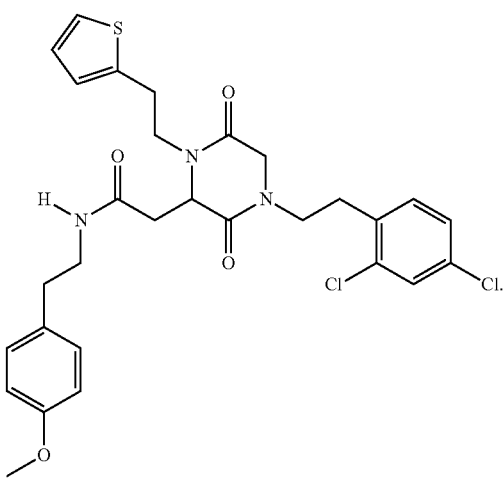

LPT98

In some forms, the active agent is a compound as described in international publication WO2011012746 of PCT Application PCT/ES2010/000349 or in international publication WO2007060524 of PCT/IB2006/003312.

In some other forms, the active agent is a compound having the structure:

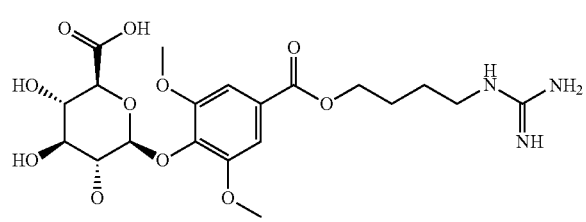

ZYZ-488

In some forms, the compositions have a concentration of the apoptosis inhibitory agent between about 125 mcg/mL and about 1500 mcg/mL, or between about 125 and about 500 mcg/mL.

In some forms, the compositions have a concentration of the apoptosis inhibitory agent (e.g. a compound containing a 1,4-piperazine-2,5-dione moiety) between about 125 µg/mL and about 1500 µg/mL. In some forms, the amount of the apoptosis inhibitory agent is between about 0.0125% w/w and about 0.15% w/w of the composition.

In a preferred embodiment, the apoptosis inhibitory agent inhibits apoptotic protease activating factor-1 (Apaf-1). Preferably, the apoptosis inhibitory agent contains a 4-piperazine-2,5-dione moiety, such as the compound 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide. In a preferred embodiment for preventing hearing loss, especially due to chemotherapeutic agents, the apoptosis inhibitory agent is 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide (LPT99), an anti-apoptosis agent that inhibits apoptotic protease activating factor-1 (Apaf-1).

B. Controlled Release Excipient

The composition, formulated for otic delivery, is in the form of a solution or suspension that effects a transition from a liquid state at room temperature to a hydrogel at body temperature. This is important so that the formulation can be injected into the inner ear, preferably using a high-gauge needle, where it then solidifies, typically through a sol-gel transition effected by the increased temperature of the body relative to the temperature at which the formulation was prepared and/or stored.

The compositions can contain additional components such as pH buffers, tonicity agents, mucoadhesive agents, stabilizing agents, preservatives, carriers, viscosity enhancing agents, and penetration enhancers.

The pH of the composition is preferably between 6.8 and 7.7, most preferably 7.2. The composition preferably has an osmolality of about 280 mOsmol/kg.

Thermosensitive Hydrogel Forming Polymers

Hydrogels are formed of networks of physically or chemically crosslinked polymers imbibed with aqueous media such as water or biological fluids. Chemical crosslinks (covalent bonds) or physical junctions (e.g. hydrophobic associations, crystallite formation, chain entanglements) provide the hydrogels' three-dimensional structure. Hydrogels have been a topic of extensive research in the past decades and their properties, such as their high water content and the possible control over the swelling kinetics. In situ forming hydrogels provide a means for wherein a polymer solution is prepared and allowed to gel in situ, after photopolymerization, chemical crosslinking, ionic crosslinking or in response to an environmental stimulus such as temperature, pH or ionic strength of the surrounding medium. Hydrogels that are sensitive to thermal stimuli are useful as temperature is the sole stimulus for their gelation with no other requirement for chemical or environmental treatment and can be thus produced e.g. upon injection to the body, when temperature is increased from ambient to physiological.

The phenomenon of transition from a solution to a gel is commonly referred to as sol-gel transition. Some hydrogels exhibit a phase transition from a liquid solution to a solid hydrogel above a certain temperature. This threshold is defined as the lower critical solution temperature (LCST). Below the LCST, the polymers exist as single chains or are associated in unpacked micelles. Above the LCST, they become increasingly hydrophobic and insoluble, leading to gel formation. Hydrogels that are formed upon cooling of a polymer solution have an upper critical solution temperature (UCST). The sol-gel transition of thermosensitive hydrogels can be experimentally verified by a number of techniques such as the vial inversion method, spectroscopy, differential scanning calorimetry (DSC) and rheology.

In some instances, intra-tympanic injection of cold compositions (e.g., a composition with temperatures of <20° C.) causes a density gradient in the inner ear fluids that induces vertigo, a phenomenon called nystagmus, in individuals undergoing prevention for inner ear disorders. Preferably, the compositions are designed to be liquids that are administered at or near room temperature and do not cause vertigo or other discomfort when administered to an individual or patient.

Some natural polymers can transition form a liquid to a solid state based on temperature, such as some of the modified cyclodextrins, but these are not preferred.

"Synthetic polymers" that transition from a liquid to solid state refers to polymers that are auris-acceptable such as copolymers of ethylene oxide and propylene oxide, (e.g., poloxamers (PLURONICS® (BASF)) such as POLOXAMER® 407 and POLOXAMER® 188). Preferred polymers are synthetic polymers such as N-isopropylacrylamide (NiPAAM) polymers, poly(ethylene oxide)-b-poly(propylene oxide)-b-poly(ethylene oxide) (PEO—PPO-PEO) as well as poly(ethylene glycol) (PEG)-biodegradable polyester copolymers. POLOXAMERS® include PLURONICS® F68, F88, F108, and F127 which are block copolymers of ethylene oxide and propylene oxide); and POLOXAMINES® (e.g., TETRONIC® 908, also known as POLOXAMINE® 908, which is a tetrafunctional block copolymer derived from sequential addition of propylene oxide and ethylene oxide to ethylenediamine (BASF Corporation, Parsippany, N.J.)), Preferred formulations contain a POLOXAMER®, triblock copolymers of poly(ethylene oxide) (PEO) and poly (propylene oxide) (PPO) available in different molecular weights and PPO/PEO ratios. The hydrogel provides sustained release of the apoptosis inhibitory agent for a period of at least 3-15 days in the ear. In a preferred embodiment, the hydrogel forming excipient is POLOXAMER® 407.

POLOXAMER® 407 (F-127) is a nonionic polymer composed of polyoxyethylene-polyoxypropylene copolymers. Other commonly used poloxamers include 188 (F-68 grade), 237 (F-87 grade), 338 (F-108 grade). Aqueous solutions of poloxamers are stable in the presence of acids, alkalis, and metal ions. PF-127 is a commercially available poly(oxyethylene)-poly(oxypropylene) triblock copolymer of general formula E106 P70 E106, with an average molar mass of 13,000 Da. In the general formula shown above, E and P denote poly(oxyethylene) and poly(oxypropylene), respectively; and the integers 106 and 70 denote the degree of polymerization of the polymers. PF-127 contains approximately 70% ethylene oxide, which provides for its hydrophilicity.

The amount of polymer, such as the thermoreversible polymer, may be about 10%, about 15%, about 20%, about 25%, about 30%, or about 35% of the total weight of the composition. In some forms, the amount of thermoreversible polymer is about 14%, about 15%, about 16%, about 17%, about 18%, about 19%, about 20%, about 21%, about 22%, about 23%, about 24% or about 25% of the total weight of the composition. In a particular implementation, the polymer is POLOXAMER® 407 at a concentration of 17.3% (w/v).

In some forms, synthetic polymers are included to enhance physical stability or for other purposes. Some other synthetic polymers include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbates such as polyethylene glycol sorbitan monostearate and polyethylene glycol sorbitan monooleate; triacetin; D-α-tocopheryl polyethylene glycol succinate (vitamin E TPGS); phospholipids; lecithins; phosphatidyl cholines (c8-c18); phosphatidylethanolamines (c8-c18); phosphatidylglycerols (c8-c18); bile salts; glyceryl monostearate; polyoxyethylene fatty acid glycerides; vegetable oils such as polyoxyethylene (60) hydrogenated castor oil; and polyoxyethylene alkylethers and alkylphenyl ethers such as octoxynol 10, octoxynol 40; or a combination thereof.

In some forms, the excipient enhances solubility of the apoptosis inhibitory agent between about, 30-fold, 100-fold, 300-fold, or 1000-fold, compared to a corresponding composition lacking the synthetic polymer or to water.

Other Additives and Excipients

Other materials can be incorporated into the hydrogel forming material. Representative materials include diluents, buffers, dispersing agents or viscosity modifying agents, solubilizers, stabilizers, and osmolarity modifying agents.

The term "diluent" refers to chemical compounds that are used to dilute, preferably, the otic agent prior to delivery, and which are compatible, preferably, with the auris media and/or auris interna.

The term "dispersing agents," and/or "viscosity modulating agents" and/or "thickening agents" refer to materials that enhance dispersion of particulate matter in a solution or modify the viscosity of a solution or suspension. Examples of dispersing agents/materials include, but are not limited to, hydrophilic polymers, electrolytes, TWEEN® 60 or TWEEN® 80, PEG, polyvinylpyrrolidone (PVP; also known as povidone and commercially known as Kollidon®, and PLASDONE®), and the carbohydrate-based dispersing agents such as, for example, modified celluloses such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), and polyethylene glycol, having a molecular weight of about 300 to about 6000, or about 3350 to about 4000, or about 7000 to about 5400. In some embodiments, the amount of thickening agent is about 1%, 5%, about 10%, or about 15% of the total weight of the composition. In some instances, dispersants improve composition stability by inhibiting drug crystallization.

The compositions have a suitable viscosity for injection through a 23-G needle or a needle of a higher gauge. At elevated temperatures (above 26° C.), the viscosity increases (due to the sol-gel transition) to above 100,000 cP. At 14.73 w/w P407, the viscosity is about 100 cP at temperatures below 20° C.

The term "solubilizer" refers to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins and other cyclodextrins, ethanol, n-butanol, isopropyl alcohol, cholesterol, bile salts, polyethylene glycol 200-600, glycofurol, TRANSCUTOL®, propylene glycol, and dimethyl isosorbide, ethanol, and other organic solvents. Preferred solvents are propylene glycol, PEG300, ethanol, and cyclodextrins.

The term "stabilizer" refers to compounds such as antioxidants, buffers, acids, and preservatives that are compatible, preferably, with the environment of the auris media and/or auris interna. Stabilizers include agents that improve the compatibility of excipients with a container, or a delivery system, including a syringe or a glass bottle, improve the stability of a component of the composition, or improve composition stability.

Tonicity and pH adjusting agents may be added. In general, the endolymph has a higher osmolality than the perilymph. For example, the endolymph has an osmolality of about 304 mOsm/kg $H_2O$, while the perilymph has an osmolality of about 294 mOsm/kg $H_2O$. In some forms, the otic or auris compositions are formulated to provide an osmolality between about 100 mOsm/kg and about 500 mOsm/kg, between about 200 mOsm/kg and about 400 mOsm/kg, between about 240 mOsm/kg and about between 350 mOsm/kg, between about 250 mOsm/kg and about 350 mOsm/kg, between about 270 mOsm/kg and about 320 mOsm/kg, or between about 280 mOsm/kg and about 320 mOsm/kg. In some forms, the compositions have an osmolality of about 280 mOsm/kg. In some forms, the compositions have an osmolarity between about 100 mOsm/L and about 500 mOsm/L, between about 200 mOsm/L and about 400 mOsm/L, between about 240 mOsm/L and about between 350 mOsm/L, between about 250 mOsm/L and about 350 mOsm/L, between about 270 mOsm/L and about 320 mOsm/L, or between about 280 mOsm/L and about 320 mOsm/L. In some forms, the osmolarity of the composition is designed to be isotonic with the targeted otic structure (e.g., endolymph, perilymph or the like).

Osmolarity/osmolality is adjusted, for example, by the use of appropriate salt concentrations (e.g., concentration of potassium salts) or the use of tonicity agents, which renders the compositions endolymph-compatible and/or perilymph-compatible (i.e., isotonic with the endolymph and/or perilymph. In some instances, the compositions, preferably endolymph-compatible and/or perilymph-compatible compositions, cause minimal disturbance to the environment of the inner ear and cause minimum discomfort (e.g., vertigo and/or nausea) to a mammal upon administration.

In some forms, the composition is isotonic with the perilymph. Isotonic compositions are provided by the addition of a tonicity agent. Suitable tonicity agents include, but are not limited to, any pharmaceutically acceptable sugar, salt or any combinations or mixtures thereof, such as, but not limited to dextrose, glycerin, mannitol, sorbitol, sodium chloride, and other electrolytes. Sodium chloride or other tonicity agents are optionally used to adjust tonicity, if necessary. Representative salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate. A preferred salt is sodium chloride.

The formulations typically include one or more pH-adjusting agents or buffering agents. Suitable pH adjusting agents or buffers include acetate, bicarbonate, ammonium chloride, citrate, phosphate, pharmaceutically acceptable salts thereof and combinations or mixtures thereof. Suitable water-soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS).

In some forms, the compositions include a mucoadhesive. Preferably, the mucoadhesive facilitates adhesion to a portion of the ear, such as the external mucous layer of the round window membrane. Mucoadhesive agents include, but are not limited to, carbomers, such as CARBOPOL® 934P, polyvinylpyrrolidone polymer (PVP); a water-swellable, but water-insoluble, fibrous, cross-linked carboxy-functional polymer; a crosslinked poly(acrylic acid) (e.g. CARBOPOL® 947P); a carbomer homopolymer; a carbomer copolymer; a hydrophilic polysaccharide gum; maltodextrin; a cross-linked alginate gum gel, hydroxypropyl methylcellulose, and a water-dispersible polycarboxylated vinyl polymer. Mucoadhesive agents are described in U.S. Pat. No. 8,828,980 to Lichter, et al.

Examples of surfactants include, but are not limited to, sodium lauryl sulfate, sodium decussate, TWEEN® 60 (polyethylene glycol sorbitan monostearate) or TWEEN®80 (polyethylene glycol sorbitan monooleate), triacetin, D-α-tocopheryl polyethylene glycol succinate (vitamin E TPGS), phospholipids, lecithins, phosphatidyl cholines (c8-c18), phosphatidylethanolamines (c8-c18), phosphatidylglycerols (c8-c18), sorbitan monooleate, polyoxyethylene sorbitan monooleate, polysorbates, bile salts, glyceryl monostearate, The compositions may include penetration enhancers that allow for delivery of the apoptosis inhibitory agents across a barrier, such as the oval window or the round window of the ear. Preferably, the penetration enhancers are auris-compatible. Penetration enhancers include sodium lauryl sulfate, sodium octyl sulfate, sodium dodecyl sulfate, ocytl-trimethyl-ammonium bromine, dodecyl-trimethyl ammonium bromide, sodium laurate, polyoxyethylene-20-cetyl ether, laureth-9, sodium dodecylsulfate, dioctyl sodium sulfosuccinate, polyoxyethylene-9-lauryl ether (PLE), TWEEN® 20, TWEEN® 80, nonylphenoxypolyethylene (NP-POE), polysorbates, bile salts, fatty acids and derivatives, chelating agents (such as EDTA, citric acid, and salicylates, sulfoxides (such as dimethyl sulfoxide (DMSO) and decylmethyl sulfoxide), and alcohols (such as ethanol, isopropanol, glycerol, and propanediol.

In some forms, the compositions include a preservative. Suitable preservatives include, but are not limited to, benzoic acid, boric acid, p-hydroxybenzoates, alcohols, quaternary compounds, stabilized chlorine dioxide, mercurials, such as merfen and thiomersal, or a combination thereof. Preservatives are described in U.S. Pat. No. 8,828,980 to Lichter, et al.

C. Concentration, pH, Tonicity of Agent in Excipient

In the preferred formulations, the formulations contain between about 0.0125% w/w and about 0.15% w/w w/w of the apoptosis inhibitor, and between about 1 µg/mL % w/w and about 10 mg/mL or alternatively 2 mg/mL % w/w, most preferably about 15-20% w/w, of the polymer such as a poly(ethylene oxide)-poly(propylene oxide) triblock copolymer having the general formula A-B-A or B-A-B, where A is poly(ethylene oxide) and B is poly(propylene oxide). The composition is in the form of a solution or suspension that effects a transition from a liquid state at room temperature to a gel state (e.g. hydrogel) at body temperature.

The resulting hydrogel provides sustained release of the therapeutic agent such as an apoptosis inhibitory agent for a period of at least about one day and 30 days, at least five days and 25 days, at least 10 days and 20 days, one day, two days, three days, four days, five days, six days, seven days, 10 days, 15 days, 20 days or 30 days, preferably at least 14 days. The same agent or different agents can be incorporated into the composition for use in single therapy or combination therapy regimens, respectively.

In some instances, the compositions are for use in the prevention and/or prevention of ototoxicity, where the compositions are formulated to provide a therapeutically effective amount of an agent such as an apoptosis inhibitor across the round window membrane into the cochlea. In the preferred embodiment, the composition contains between about 50 µM and about 1000 µM of the apoptosis inhibitor, or pharmaceutically acceptable prodrug or salt thereof; between about 10% and about 30% by weight of a poly (ethylene oxide)-poly(propylene oxide) triblock copolymer of general A-B-A or B-A-B, where A is poly(ethylene oxide) and B is poly(propylene oxide). In some embodiments, the composition includes about 797 µM of an apoptosis inhibitor, wherein the inhibitor is an Apaf-1 inhibitor. In another embodiment, the Apaf-1 inhibitor is 2-(4-(2,4-dichlorophen-ethyl)-3,6-dioxo-1-(2-(thiophen-2-yl)ethyl)piperazin-2-yl)-N-(2-(5-methoxy-1H-indol-3-yl)ethyl)acetamide.

Compositions for use in the prevention and/or prevention of ototoxicity are formulated to provide a therapeutically effective amount of an agent such as apoptosis inhibitor across the round window membrane into the cochlea, contain between about 100 µg/mL and about 500 µg/ml and about 1500 µg/ml of an apoptosis inhibitor, or pharmaceutically acceptable salt thereof. In a specific embodiment, the composition includes between about 100-500 µg/mL of an Apaf-1 inhibitor such as 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide.

The pH of the composition is between 6 and 8, between 6 and 7.6, more preferably between 6.8 and 7.5, and most preferably 7.2.

In some forms, the composition includes other therapeutic, prophylactic and/or diagnostic agents.

The composition can be prepared and stored in vials, syringes, capsules, ampules, or pouches prior to administration. The composition may be packaged in a single-dose that is administered intra-tympanically into the middle ear. Formulations may be lyophilized, micronized, pelleted, or in a solution or suspension. Optionally, the components of the composition are provided in kits that contain instructions to formulate the composition by adding diluent to excipient and/or agent.

III. Methods of Making

Preferably, the composition is prepared by mixing an effective amount of an active ingredient, to prevent hearing loss, in a gel forming solution.

Since the polymer systems of the thermoreversible gel dissolve more completely at reduced temperatures, the preferred methods of solubilization are to add the required amount of polymer to the amount of water to be used. Generally, during or after wetting the polymer by shaking, stirring, or otherwise mixing, the mixture is maintained for some time between about 0° C. and 10° C. in order to dissolve the polymer. The mixture can be stirred or shaken to bring about a more rapid dissolution of the polymer. Cosolvents can be used to enhance drug solubility; however, some drugs exhibit poor aqueous solubility. These can often be suspended in the polymer vehicle with the aid of suitable suspending or viscosity enhancing agents.

The agent and various excipients such as buffers, salts, and preservatives can subsequently be added to the polymer-containing gel and dissolved. In some forms the agent is suspended if it is insoluble in water. If needed, the pH can be modulated by the addition of appropriate buffering agents. Depending on the concentration of the agent, it can exist as micronized particles in the composition. Preferably, a phosphate buffer is prepared and sterile filtered, and the synthetic polymer is slowly added to cold buffer with stirring, and refrigerated overnight.

IV. Methods of Using

The formulations are administered to the inner ear of a subject in need thereof. Typically, the subject to be treated is an adult or pediatric human undergoing treatments that can cause hearing loss, such as chemotherapy, hearing loss due to aging, hearing loss due to repeated exposure to loud noises, and other disorders damaging the cilia in the inner ear such as autoimmune disorders, infection, excess fluid or pressure.

In general, methods of use involve administering to the subject by injection compositions containing an effective amount of the apoptosis inhibitory agent(s) to prevent hearing loss associated with exposure to ototoxic agents, such as chemotherapeutics, exposure to loud noise. The formulation can also be used to prevent hearing loss due to exposure to loud noise; aging; or autoimmune inner ear disease but must have longer duration for treatment, such as through administration via a reservoir or depot. The composition can be administered before, during, or after exposure to an insult associated with hearing loss, but are most effective if administered prior to hearing loss.

Preferred methods of administration of the composition are localized administrations by intra-tympanic injection of the formulation as a solution (i.e., at room temperature or lower) or suspension. Such administration routes and appropriate compositions are generally known to those of skill in the art. After administration, the composition effects a transition from a liquid state at room temperature to a gel state at body temperature. Preferably, the gel state provides sustained release of the apoptosis inhibitory agent for a period of least about one day and 30 days, at least five days and 25 days, at least 10 days and 20 days, one day, two days, three days, four days, five days, six days, seven days, 10 days, 15 days, 20 days or 30 days, preferably at least 14 days.

In the preferred embodiment, the compositions are administered on or near the round window membrane via intra-tympanic injection. The composition may also be administered on or near the round window or the crista fenestrae cochleae through entry via a post-auricular incision and surgical manipulation into or near the round window or the crista fenestrae cochleae area. Preferably administration is made using a syringe and small gauge needle, 23G to 30G or higher gauge, wherein the needle is inserted through the tympanic membrane. The composition fills the hypotympanum of the tympanic cavity, and contacts the round window membrane, for localized prevention of hearing loss. In other embodiments, the composition is administered via microcathethers implanted into the subject, using a drug delivery device such as a micropump, a microinjection device, or a microreservoir implanted within the inner ear for long term prevention of hearing loss.

The formulation can also be administered into the tympanic cavity or applied on the tympanic membrane or onto or in the auditory canal by injection, direct instillation or perfusion of the inner ear compartments, or in surgical procedures including, mastoidectomy, and stapedectomy. In some instances, the formulation may be directly injected into the cochlea via injection through the round window membrane or a cochleostomy drilled in the bone of the cochlea.

The compositions can be administered in a single dose or in multiple doses. Certain factors may influence the dosage required to effectively treat or prevent a disorder, including, but not limited to, recurrence of the cochlear insult, the severity of the disease or disorder, previous preventions, the general health and/or age of the subject, and other diseases present. It will also be appreciated that the effective dosage of the composition used for prevention may increase or decrease over the course of a particular treatment time period. Need for changes in dosage quantity or strength may result become apparent from the results of assays, for example the auditory brainstem response, distortion product otoacoustic emission, and word recognition scores, or subjective changes in hearing reported by the patient.

In some forms, the clinical dosing regimen can be a single, unilateral, intra-tympanic administration of an apoptosis inhibitor. The apoptosis inhibitor can be an Apaf-1 inhibitor. In some forms, the Apaf-1 inhibitor is 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide, delivered in a volume of between about 0.05 and 0.5 mL, most preferably 0.2 mL liquid formulation.

For the calculation of the maximum recommended starting dose (MRSD) the following parameters have been considered:

The mass of injected LPT99 at the no observed adverse effect level in the rat (NOAEL) is 15 µg (30 µl of 797 µM)

There is currently no published reference of the total volume of perilymph volume in rats. However, the cochlear volume of perilymph in rats has been reported to be 2.63 µl ($ST_{perilymph}+SV_{perilymph}=1.04+1.59=2.63$ µl, ST: scala tympani; SV: scala vestibule) as described in Thorne, et al., Laryngoscop 109(10), 1661-8 (1999).

The volume of perilymph in the rat semicircular canals was estimated. A cylinder shape was assumed for the semicircular canals following the method described in Buckingham and Valvassori, Ann. Otol. Rhinol. Laryngol. 110(2), 113-7 (2001) for humans and the dimensions for the semicircular canals in rat described in Cummins, J. Comp. Neurol. 38, 399-459 (1925). The total volume has been calculated as: $V=\pi \times r^2 \times l$ (r: radius; l: length). The estimated volume for each canal is:

Anterior: 0.33 mm³ ($\pi \times 0.125^2 \times 6.8$): 0.33 µl
Posterior: 0.31 mm³ ($\pi \times 0.13^2 \times 6$): 0.31 µl
Lateral: 0.26 mm³ ($\pi \times 0.125^2 \times 5.4$): 0.26 µl The total perilymph volume in rat will be then: (Cochlear$_{perilymph}$+Semicircular canals$_{perilymph}$)=ST$_{perilymph}$+SV$_{perilymph}$+Semicircular canals$_{perilymph}$=1.04+1.59+0.9=3.53 µl The total perilymph volume in human has been described to be 158 µl (Buckingham and Valvassori, Ann. Otol. Rhinol. Laryngol. 2001, 110(2), 113-7).

The amount of LPT99 to be injected in humans is normalized with the volumes of perilymph in rats and humans and the amount injected at the NOAEL dose as follows:

LPT99 injected,$_{rats}$/Volume perilymph$_{rats}$=LPT99 injected,$_{humans}$/Volume perilymph$_{humans}$ 15 µg/3.53 µl=$Y$ µg/158 µl; $Y$=671.38 µg.

MRSD should not exceed that which is calculated to deliver ¹/₁₀th of the estimated perilymph concentration of LPT99 in rat at the NOAEL, when normalized to the perilymph volume in humans. 67.14 µg (¹/₁₀ of 671.38 µg) is calculated as the maximum mass of LPT99 to be delivered in a volume of 200 µl. The MRSD would be then 67.14 µg/200 µl=535 µM.

The resulting estimated clinical doses are 200 µM, 400 µM, 600 µM and 797 µM. The two lowest concentrations to be studied in the clinical trials are below the MRSD. The two lowest concentrations to be tested are below the MRSD.

The present invention will be further understood by reference to the following non-limiting examples.

EXAMPLES

The data presented in the non-limiting examples below show the efficacy of an apoptosis inhibitor, specifically the Apaf-1 inhibitor LPT99, in the prevention and/or prevention of ototoxicity such as, but not limited to, ototoxicity caused by platinum-based chemotherapeutic agents.

Example 1: Preparation of Hydrogel for Loading 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide (LPT99)

In vitro experiments with LPT99 demonstrated its specificity for Apaf-1, resulting in inhibition of apoptotic protease activating factor-1 (Apaf-1). In a cellular model of CisPt-induced apoptosis, LPT99-treated cells showed a decreased release of Cytc from mitochondria, reduced caspase-3 activation, and an improved cell viability, evidence of the cytoprotective effect of LPT99 (Cervantes, et al., IEB Symposium, Montpellier, Abstract P77, "Inhibition of APAF-1 with LPT99 prevents cisplatin-induced apoptosis in HEI-OC1 auditory cells", Sep. 18, 2016; Maurillo-Cuesta, et al., IEB Symposium, Montpellier, Abstract P78, Inhibition of Apaf-1 with LPT99 prevents cisplatin-induced hearing loss, Sep. 18, 2016).

These studies showed that the compound LPT99 could be effective in preventing hearing loss due to exposure to cisplatin in vitro in cell culture, if a formulation could be developed for administration in a single injection which would provide protection during a portion, or preferably a majority of the duration of the cochlear insult.

Materials and Methods

In order to effectively deliver LPT99 to the cochlea, an otic extended release composition, specifically, a hydrogel composition for loading LPT99, which becomes a solution after loading LPT99, was developed which was suitable for injection into the inner ear, where it forms a sustained release hydrogel.

For the preparation of buffer, the reagents were weighed one by one on a precision balance inside the laminar flow cabinet. Table 1 below details the composition of the buffer in units of g/L.

TABLE 1

| Phosphate buffer composition | |
| --- | --- |
| Composition | (g/L) |
| Hydrogen phosphate di-sodium dodecahydrate | 0.6 |
| Dihydrogen sodium phosphate dihydrate | 0.05 |
| Sodium chloride | 0.4 |
| Water for Injection (WFI) | c.s.p. |

First, around 150 ml of water for injection (WFI) was added to a 280 mL beaker and kept under magnetic stirring. The reagents were then added as follows:

0.05 g of Dihydrogen sodium phosphate dihydrate are weighed into an aluminum weighing pan (WPAL-072-100) and added to the WFI being stirred. To ensure that everything was added, the rest of the reagent that can remain on the weighing pan is washed with WFI.

The same procedure was followed to add hydrogen phosphate di-sodium dodecahydrate and Sodium chloride. After all reagents were weighed and added, the buffer was kept under magnetic stirring in the beaker for 15 minutes. After this time, the solution was passed to a 1 L volumetric flask. The solution was kept under magnetic stirring for 1 h, to ensure that the salts have completely dissolved.

After one hour of stirring, the magnetic rod was removed from the volumetric flask and the flask is levelled to obtain 1 L of buffer. Finally, the buffer was filtered through a sterile filter of 0.22 µm (Top-Filter Nalgene, 90 mm, pore 0.2, 500 mL, thread GL45) with the help of a vacuum pump.

The preparation of the hydrogel was carried out inside the laminar flow cabinet located in a cleanroom. Table 2 below details the composition of the P407 hydrogel in units of g/L.

TABLE 2

| Composition of the P407 hydrogel in units of g/L | | |
| --- | --- | --- |
| P407 Hydrogel Composition | Gel P407-14.73% (w/w) (g/L) | Function |
| POLOXAMER ® 407 | 173 | Thermogelling agent |
| Hydrogen phosphate di-sodium dodecahydrate | 0.6 | Buffer pH |
| Dihydrogen sodium phosphate dehydrate | 0.05 | Buffer pH |
| Sodium chloride | 0.4 | Osmolarity modifier |
| Water for Injection (WFI) | 1000 (no QS to 1000 mL) | Solvent |

P407 14.73% (w/w gel) was prepared by the slow addition of P407 to a cold buffer solution (NaH$_2$PO$_4$.2H$_2$O 0.05 g/L, NaHPO$_4$.12H$_2$O 0.6 g/L, NaCL 0.4 g/L, pH 7.4), and maintained on a roller stirrer at 4-8° C. for 6 h.

To prepare 100 mL of the hydrogel, first a sterile 250 ml borosilicate glass lab bottle was placed in the precision balance and it was tared. Then, 17.3 g of P407 were weighed in the tared bottle and 100 mL of the previously prepared cold phosphate buffer was added. Finally, the solution was stirred, initial strong stirring was carried out for 60 seconds to facilitate the dissolution of P407, and then it was kept under stirring on a roller stirrer at 30 rpm for 6 hours in a refrigerator. After 6 h, the P407 was completely dissolved, and was left in the refrigerator overnight so that the foam generated during the stirring process will disappear.

The hydrogel was stored in a refrigerator at a temperature between 2° C. and 8° C., until use.

The loading of LPT99 was produced by forming a homogeneous solution of the drug in the P407 14.73% w/w vehicle. Briefly, to prepare 20 ml of a 300 µg/mL solution of LPT99 in P407 14.73% (w/w) gel, a sterile 20 ml amber glass vial was first placed on the precision balance and it was tared. Then, 6 mg of LPT99 was weighed in the tared vial and 20 ml of the previously prepared cold P407 14.73% w/w vehicle was added. Finally, in order to obtain a solution as homogeneous as possible, it was stirred in an ultrasonic bath for a time frame between 40 seconds and 60 seconds, until a homogeneous and free of lumps solution was obtained.

Samples were kept under refrigeration (typically 4° C.) and resuspended before using.

Once the solution of LPT99 was prepared and homogenized, it was dosed in different vials for later use. It was very important to keep vials cold during dosification. If the product thickens during preparation, the vial should be placed back in the refrigerator. The vial should be held by the cap to prevent gelation due to temperature transition.

Before dosing the product from one vial to another, e.g. empty sterile vial, the vial containing the solution was shaken to mix its contents until a visually homogeneous solution was obtained. Then, with the aid of a micropipette, the solution was pipetted several times to mix and withdraw a homogeneous sample, and 1000 µL of the solution was removed and added to the empty sterile vial. This action was repeated each time the sample was withdrawn. It is important to hold the vial by the cap to prevent gelation.

Example 2: Analysis of the Final Product

The viscosity measurement of the hydrogel was performed to determine the behavior of the viscoelastic agent once gelled within the ear. The measurement was carried out following the European Pharmacopoeia Method, section 2.2.10 (measured at 37° C., body temperature).

P407 is a thermoreversible compound, existing in a liquid or gel state depending on its temperature. Accordingly, it can form a semi-solid gel at body temperature of 37° C., being liquid at room temperature. During the development process, this allowed formation of an easy to handle solution with the LPT99 molecule, which gels at 37° C., once the solution is administered to a patient.

Viscosity measurements were performed at 37° C. to simulate the real conditions of application of the gel, once it has gelled. The solution was first placed in a climatic chamber at 37° C. to gel (20 mL of solution for about 1 h), and once gelled, the viscosity was measured by maintaining this temperature with a thermostat bath (temperature control equipment for viscosity measurements). The gelation of the product was carried out in a 20-mL syringe to facilitate the incorporation of the gel into the sample chamber of the viscometer, once gelled.

The viscosity measurement was performed with a Rotational Viscometer (FungiLab/Evo Expert). The viscosity measures vary depending on the temperature. That is why the temperature was controlled by the temperature probe of the viscometer, keeping it at 37° C. To achieve this temperature, the viscometer was connected to a thermostat bath. The equipment used depends on the viscosity of the gel. This viscosity determines the spindle and adapter to be used. Also depending on the spindle used, a quantity of sample is required as well as a speed of rotation (RPM) to reach SR=1 s−1.

The following equipment was used:

| P407 concentration | Viscosimeter | Adapter | Spindle | sample volume (mL) | RPM (SW≈4s-1) |
|---|---|---|---|---|---|
| 14.73% (w/w) | EvoExpert R (10026) | APM (small sample adapter) with thermostatation jacket | TR11 | 13.5 | 4 |

The sample chamber of the low sample amount adapter was filled with 13.5 ml sample. After filling the sample chamber, the spindle was inserted (TR11 in this case). Since the penetration of the spindle alters the surface of the gel, it was necessary to allow the sample to stabilize before measuring (approximately 30 min). The sample should be free of bubbles, as these could distort the measurement. The measurements were carried out at 1 s-1 shear rate (SR). For this, the spindle is programmed so that it turns to the corresponding RPM (4 rpm in this case). Finally, the measurement time was programmed (in seconds, 3600 sec equivalent to 1 h of measurement) and after that time a graph showing the viscosity (cp) versus time (sec) at $1\ s^{-1}$ SR at 37° C. is obtained.

pH measurements were performed to ensure that it is maintained in the physiological range for the indicated application. A Crison pH-meter was used and the measurement was carried out following the European Pharmacopoeia Method, section 2.2.3, after calibrating the equipment following the indications of the apparatus. The pH should be maintained in the range 7-7.5, most preferably 7.2.

Osmolality measures were performed to ensure that it is maintained in the physiological range for the indicated application. The determination of the Osmolality was carried out by means of a cryogenic osmometer following the European Pharmacopoeia Method, section 2.2.35, and is preferably maintained in the range between 240 mOsmol/kg and 350 mOsmol/kg.

Figure 1:
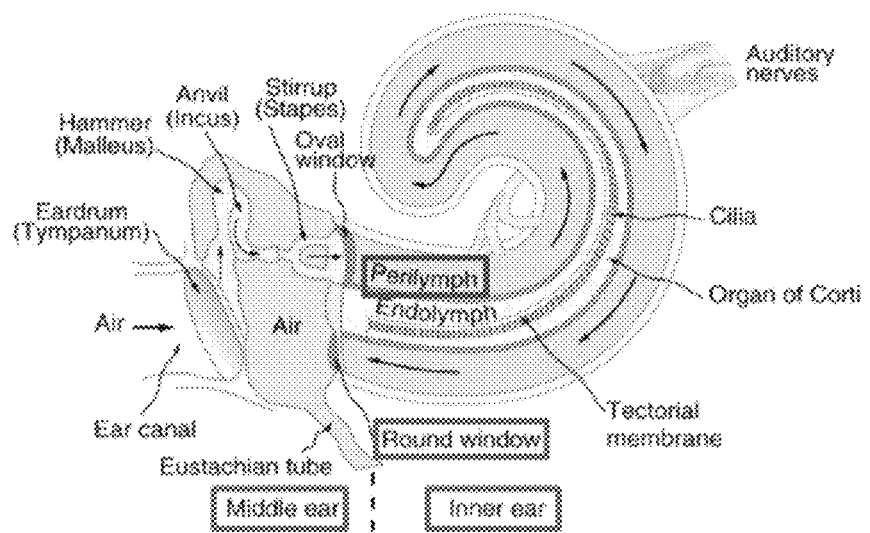
FIG. 1 is a cross-sectional view of the anatomy of the middle and inner ear.

The in vitro release assay was performed using cellulose dialysis membranes of 3500 Da (OrDial D35-MWCO 3500, Orange Scientific) to simulate the round window membrane, located between the middle ear and the inner ear, as it is the first barrier for the drug to reach the inner ear where it will exert its pharmacological action. (See FIG. 1) Artificial perilymph (NaCl 137 mM, KCl 5 mM, $CaCl_2$ 2 mM, $MgCl_2$ 1 mM and $NaHCO_3$ 1 mM) was used to simulate the environment inside the inner ear, since this is the liquid that interact with the drug after crossing the round window. The assay was performed at 37° C., continuing with the simulation of ear conditions.

Table 3 details the composition of the artificial perilymph in units of g/L:

TABLE 3

Composition of the artificial perilymph in g/L

| Composition | (g/L) |
| --- | --- |
| Sodium chloride | 8.006 |
| Potassium chloride | 0.373 |
| Calcium chloride | 0.222 |
| Magnesium chloride | 0.095 |
| Sodium bicarbonate | 0.084 |
| Type II Water | c.s.p. 1L |

For the preparation of the artificial perilymph, the reagents were weighed one by one on a precision balance. A 250 ml beaker was placed with around 150 ml of Type II Water and kept under magnetic stirring. The reagents were then added as follows: first, 8.006 g of sodium chloride was weighed into an aluminum weighing pan (WPAL-072-100) and added to the Type II water being stirred. To ensure that everything was added, the rest of the reagent that remained on the weighing pan was washed with water. The same procedure was followed to add the rest of the reagents. After all reagents were weighed and added, the buffer was kept under magnetic stirring in the beaker for 15 minutes. Next, the solution was passed to a 1 L volumetric flask and type II water was added but without levelling the flask. The solution was kept under magnetic stirring for 1 h, to ensure that the salts were completely dissolved. After one hour of stirring, the magnetic rod was removed from the volumetric flask and the flask was leveled to obtain 1 L of artificial perilymph.

To prepare the release assay, ten (10) mL of the LPT99 loaded hydrogel was placed inside a 3500 Da dialysis membrane, the membrane with the hydrogel was introduced into a 100 ml borosilicate glass lab bottle and 30 ml of artificial perilymph was added. All samples were kept under magnetic stirring at 37° C. Due to the thermo-reversible behavior of P407, firstly the hydrogel was deposited into the membrane at 37° C. and left to harden. Once it gelled, the artificial perilymph was added and kept under stirring at 37° C.

Samples were taken at different time points (1 h, 3 h, 6 h, 1 day, 2 days, 3 days, 6 days, 7 days, 8 days, 9 days, 10 days, 13 days, 14 days and 15 days) at which time 5 mL were withdrawn with a graduated glass pipette and replaced with equivalent volume of artificial perilymph. The collected samples were analyzed to determine the amount of drug released from the hydrogel at each time point.

Analytical Method for the Quantification of the Released LPT99

For the analysis of LPT99 released from the hydrogel, samples analysis was performed using a High-Performance Liquid Chromatography with Diode-Array Detection (HPLC/DAD) (Agilent) with a calibration curve in the range of 0.2-20 ppm. The collected samples were previously purified using solid phase extraction C18 (SPE C18) cartridges.

LPT99 molecule presents spectroscopic activity in the UV range, at wavelengths between 200 nm and 280 nm. Quantification by HPLC-DAD is a suitable method in the absence of interfering compounds.

For the LPT99 analysis, an Agilent 1290 Infinity UHPLC liquid chromatograph (Agilent Technologies, Waldbronn, Germany) equipped with a diode array detector (DAD), an autosampler, an automatic injector, and a column oven were utilized. As stationary phase, a Zorbax Eclipse Plus C18 rapid resolution column (50×2.1 mm, 1.8 m particle size, Agilent) guarded with an in-line filter (0.3 m pore size frit, 2.1 mm diameter, Agilent) kept in a column oven at 30° C. was used. Water (A) and acetonitrile (B), each containing 0.1% formic acid (v/v), served as mobile phases eluting at a flow rate of 0.6 ml/min. The gradient was t=0.0 min, /0% A; t=0.3 min, 70% A; t=7 min, 30% A; t=8.5 min, 30% A; t=9 min, 70% A; t=10 min, 70% A. Between runs, the column was equilibrated with 70% A for 1 min. The injection volume was 1 µl and chromatograms were recorded at 230 nm and 278 nm.

Calibration Curve Prepared Directly in MeOH

For direct LPT99 quantification, an external calibration curve of LPT99 was prepared in methanol (MeOH) in the range of 0.2-25 ppm, starting from a 100 ppm stock solution which was diluted with MeOH to obtain various standards of the curve. The analysis of the blank showed no absorbance in the range of the considered wavelengths. The coefficient of regression of the curve was R2=0.996 indicating good linearity in the concentration range tested. (See FIG. 2B) This quantification method was therefore appropriate if the sample is free of interference, so a suitable extraction process was necessary.

Solid Phase Extraction (SPE)

This method was performed for extracting LPT99 from perilymph samples (samples of perilymph with the LPT99 released from the hydrogel during the in vitro release assays).

The separation was performed using Hypersep C18 solid phase extraction cartridges (500 mg, 3 mL) from Thermo scientific (Rockwood, USA). Conditioning of the cartridge was carried out with methanol (MeOH), followed by cleaning the samples by $H_2O$. The drug was eluted with MeOH, evaporated and reconstituted with MeOH for its quantitation by HPLC-DAD.

The extraction method was optimized by adjusting the load volumes to ensure that the amount of drug retained in the stationary phase was the highest possible. The volumes of water used in the cleaning phase were adjusted to ensure an effective elimination of interfering components avoiding the loss of retained analyte. Finally, the volume of MeOH used as eluent was adjusted to achieve a complete elution of LPT99 in the smallest possible volume, thereby causing the pre-concentration of the analyte and an improvement of the signal obtained in the HPLC-DAD.

A vacuum manifold from Varian (Palo Alto, USA), connected to a vacuum pump was used for the solid phase extraction (SPE) process. Before analysis, dry cartridges were first conditioned by percolating 5 mL of methanol, followed by 5 mL of water. Five (5) mL of sample (or standard) were subsequently loaded and cartridges were then washed with 20 mL of water, in order to remove the remaining polymer. The target compound was recovered eluting the SPE column with 1 mL of methanol.

Calibration Curve Prepared after the Extraction Process

A calibration curve was prepared in the concentration range of 0.2-20 ppm starting from a 500 ppm stock solution, but it was diluted with perylimph from a pool of blank samples (absence of LPT99) to obtain various standards of the curve. These standards were subjected to an extraction process using HYPERSEP® C18 solid phase extraction cartridges (500 mg, 3 mL) from Thermo scientific (Rockwood, USA). To avoid any solubility problem of the target compound in perylimph, 0.5 ml methanol was added to the standards and the samples before extraction. The coefficient of regression of the curve was R2=0.999 indicating good linearity in the concentration range tested.

Results

Figure 2A:
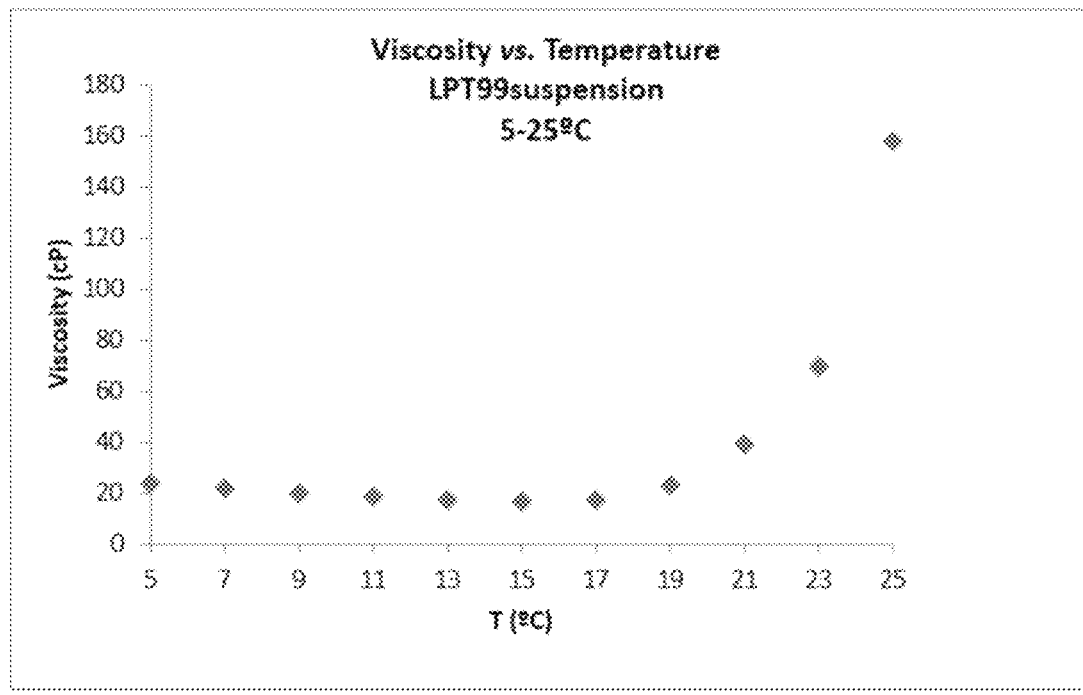
FIG. 2A-2B are graphs of temperature-induced gelation of LPT99-H1 in a POLOXAMER solution, viscosity (cP) versus temperature (° C.).
Figure 2B:
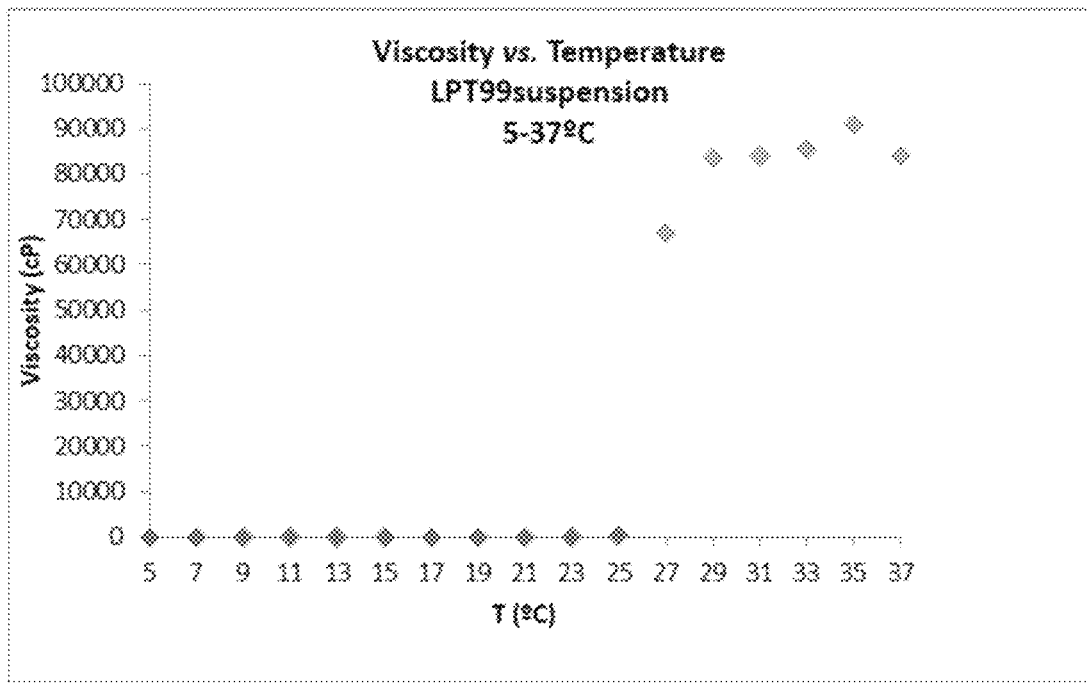

FIGS. 2A and 2B demonstrate the formation of thermoset gels under in vivo conditions, showing how the formulation goes from a liquid which can be administered by injection at room temperature (15-25° C.) to a semi-solid hydrogel at body temperature (37° C.).

Figure 3A:
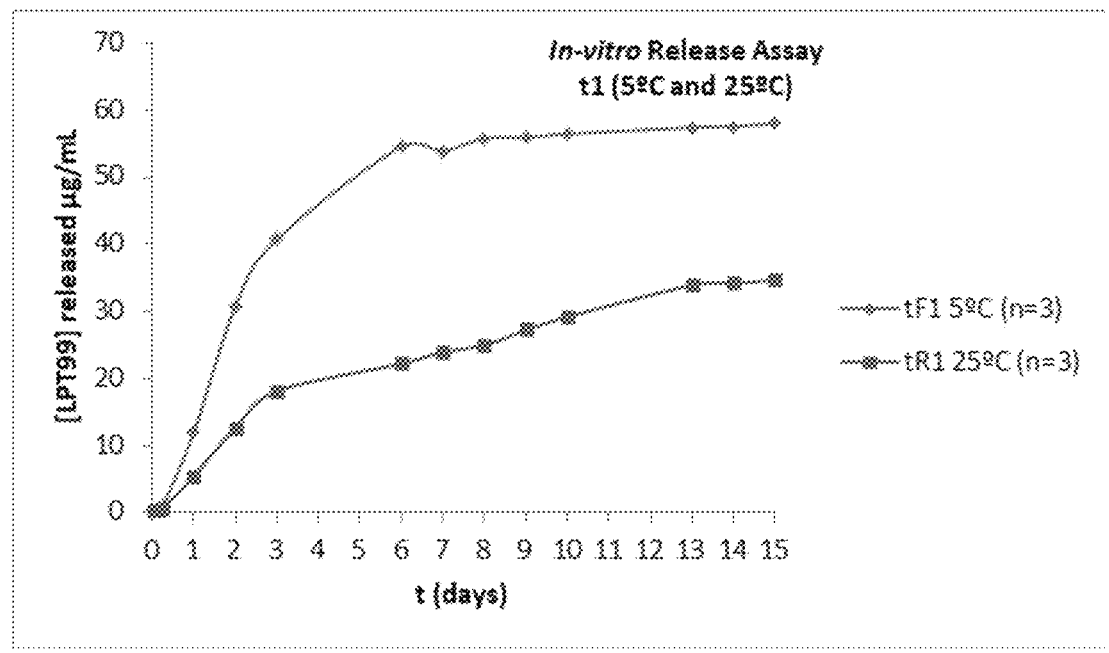
FIG. 3A-3B are graphs of LPT99 release (FIG. 3A, µg/g.
Figure 3B:
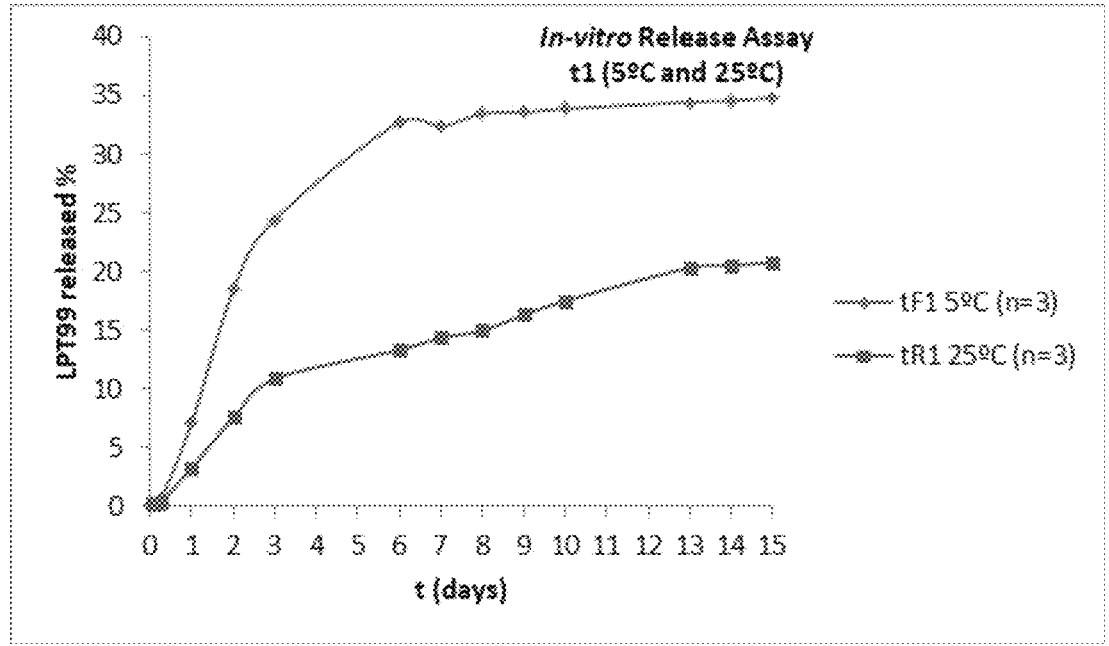

FIGS. 3A and 3B demonstrate that the drug, LPT99, is released over time (days) in a controlled manner. FIG. 3A shows release as a function of amount (µg/ml). FIG. 3B shows release as a percent of total drug. The drug is released in effective amounts for at least one week.

Example 3: In Vitro Studies Showing Efficacy of Formulation

Materials and Methods

The specificity of LPT99 was tested in vitro on Apaf-1, caspase 3, and caspase 9 (proteins from the apoptotic cascade), and a broad panel of potential pharmacological targets.

To identify off-target activities of LPT99, its selectivity against a panel of receptors (44 G-protein-coupled receptors [GPCR] and 4 non-GPCR), 4 ion channels, and 3 transporters were analyzed. The cell line, HEI-OC1 (house ear institute organ of Corti 1), which expresses several characteristic markers of the organ of Corti sensory cells (Kalinec, et al., Audiol. Neurootol. 2003, 8(4), 177-89), was used to evaluate the efficacy of LPT99 in preventing apoptosis due to CisPt prevention. Cells were pre-incubated with LPT99, followed by CisPt prevention for 24 hours. Under these conditions, the 50% inhibitory concentration ($IC_{50}$) for caspase 3 was 5.2±1.6 µM. Both LPT99 stereoisomers were equally effective and equivalent to the racemic mixture, suppressing caspase 3 activation in the cellular model.

Flow cytometry was also used to characterize the effect of LPT99 in the release of mitochondrial Cytc in HEI-OC1 cells in vitro with CisPt prevention.

Results

LPT99 inhibited the formation of the apoptosome complex composed by recombinant Apaf-1, Cytc, deoxyadenosine triphosphate (dATP), and caspase 9. This activity was measured as inhibition of caspase 3 activation. At 10 µM, the LPT99 apoptosome inhibition was (mean %±standard deviation [SD] %) 78.9%±12.7%. To evaluate the specificity of the inhibition, an assay of caspase 3 and 9 activation was set up with recombinant proteins. The inhibitions of caspase 3 and 9 were 7.6±14.7 and 5.3±3.5, respectively, for LPT99. These results probed the specificity of LPT99 on Apaf-1 inhibition among other components of the apoptotic cascade.

The in vitro inhibition obtained for 41 of these tested targets was <50% at 10 µM, indicating that LPT99 had no affinity for them. For 14 of the tested targets-adenosine receptor 3 (A3); cholecystokinin: cholecystokinin receptor 1 (CCK1); melatonin receptor (MT1); neurokinin (NK2 and NK3); opioid (kOP and mOP); serotonin receptors ($5HT_{1A}$, $5HT_{2A}$, $5HT_{2B}$ and $5HT_7$); and vasopressin (ViA; Na+channel site 2 and Cl-GABA-gated channel)—the LPT99 affinity was >50%. At 1 µM, the inhibition of 13 of these targets was <50%, indicating a very low affinity with LPT99. Inhibition of MT1 was 53% at 1 µM and 6% at 0.1 µM, showing a low affinity of LPT99 for this protein. These results confirmed the LPT99 specificity for Apaf-1 inhibition. Moreover, because no LPT99 has been found in plasma after IT administration of the LPT99 formulation in a hydrogel; detection limit at 2 ng/mL=3.2 nM), no side effects due to these low-affinity interactions were expected.

In vitro experiments with a 2,5-piperazinedione derivative showed suppression of caspase 3 activation in vitro, distribution to the cochlea after intratympanic administration in a dose dependent manner, and protection from apoptosis as well as maintenance of cell viability after CisPt prevention. In vitro experiments with LPT99 demonstrated the drug's specificity for Apaf-1, resulting in its inhibition.

In a cellular model of CisPt-induced apoptosis, LPT99-treated cells showed a decreased release of Cytc from mitochondria, reduced caspase-3 activation, and improved cell viability, showing the cytoprotective effect of LPT99.

LPT99 inhibited release of mitochondrial Cytc from 28%±6.6% after CisPt prevention to 68.1%±1.0% in cells that had been pre-incubated with LPT99). This dual inhibitory effect of LPT99 resulted in increased cellular viability with CisPt prevention. Prevention with CisPt (0 to 5 µg/mL) resulted in a dose-dependent decrease in HEI-OC1 cell viability ($IC_{50}$=4.47±1.94 ag/mL). Survival rate increased in the presence of 1 µM LPT99, with an $IC_{50}$ of 10.51±3 µg/Ml. The effect of LPT99 on proliferation of non-apoptotic cells was studied. A549 cells were cultured in the presence of LPT99 for up to 6 days; the cell number was monitored by flow cytometry, and doubling time was calculated. The Apaf-1 inhibitor delayed cellular proliferation by accumulation of cells at the GI phase of the cell cycle; if the Apaf-1 inhibitor was removed from the medium, this effect was reversible. These results indicated that Apaf-1 pharmacological inhibition in nonapoptotic cells did not increase the cellular proliferative rate in vitro.

Example 4: Dose Development

Materials and Methods

During nonclinical development studies, the following dose nomenclature for LPT99 was presented, as shown in Table 4.

TABLE 4

Dose nomenclature for LPT99 solution

| Dose (µg/mL) | Equivalent Dose (µM) |
|---|---|
| 32 | 50 |
| 63 | 100 |
| 300 | 478 |
| 500 | 797 |

Results

Figure 4:
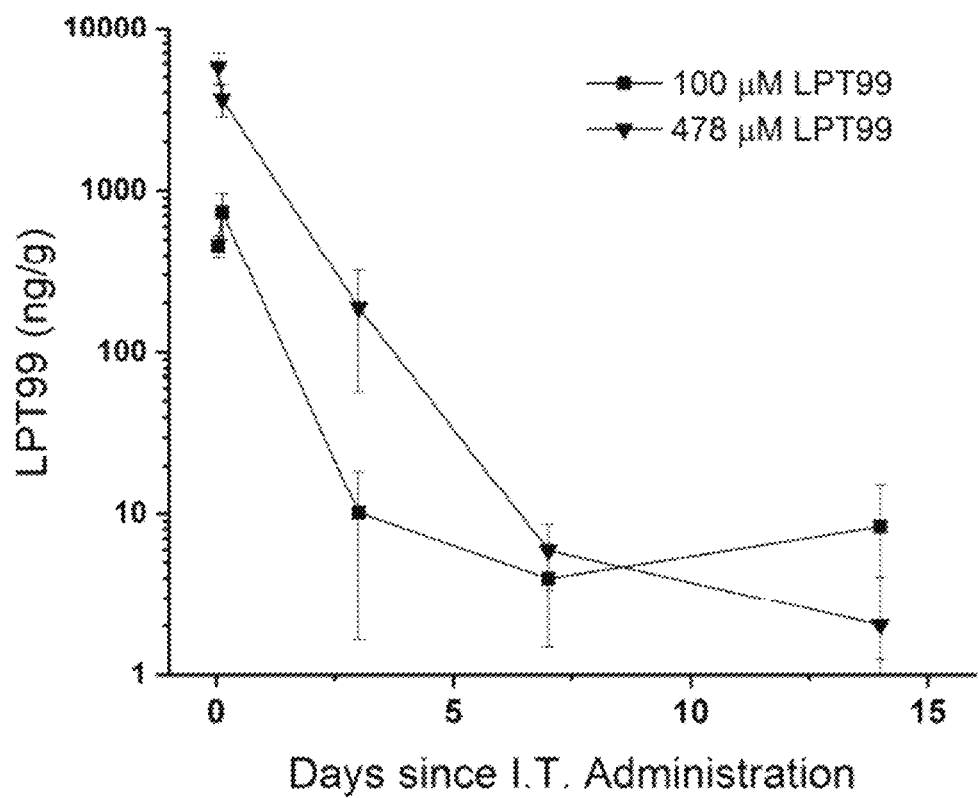
FIG. 4 is a graph of LPT99 concentration (ng/g) over days since intratympanic injection of 100 and 478 µM LPT99.

In vivo experiments in rats showed that, after intratympanic (IT) administration of LPT99 in hydrogel, LPT99 distributed locally to the cochlea. See FIG. 4. The safety of IT administration was also confirmed, as LPT99 levels that could offset CisPt efficacy were not detected systemically. LPT99 IT administration protected against CisPt-induced hearing loss, when compared with the vehicle control This effect was dose dependent; the group prevented with CisPt plus LPT99 showed significantly lower auditory threshold shifts than seen in the CisPt control group.

Example 5: In Vivo Efficacy in Preventing Hearing Loss

Materials and Methods

A model of CisPt-induced hearing loss in rats was evaluated to test the in vivo efficacy of LPT99. Ototoxicity was induced by intraperitoneal (IP) slow infusion of CisPt at doses that compared with those used in human preventions (eg, 10 mg/kg). LPT99 was administered IT 30 minutes before CisPt was given. LPT99 was prepared in 2 compositions: a solution in 5% HPβCD in physiological serum (LPT99-CD), and a POLOXAMER® 407-based thermoreversible hydrogel (LPT99 solution).

The protective effect of LPT99 was evaluated 3 days after CisPt administration by functional measures, such as auditory brainstem response (ABR) threshold shift, DPOAE, and expression of biomarkers of apoptosis in cochlea and cytocochleograms.

Results

Figure 5A:
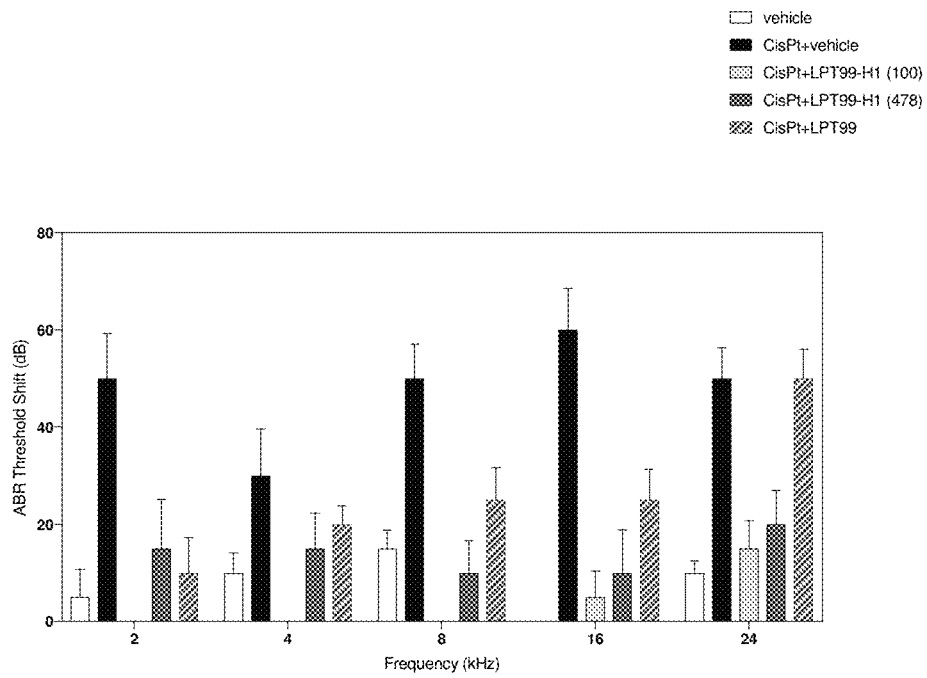
FIG. 5A-5B are graphs of LPT99 concentrations within cochlea harvested and rinsed at several timepoints after intratympanic injection of drug product (5A, left ear; 5B, right ear). Drug concentration in cochlear homogenates is expressed as nanograms LPT99 per gram of cochlear homogenate.
Figure 5B:
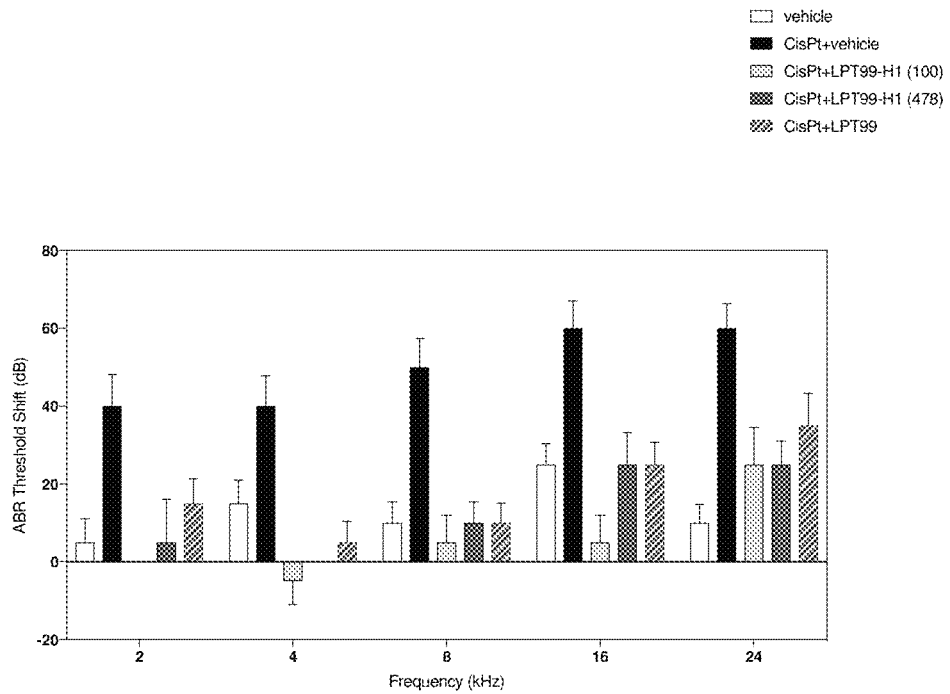

Intra-tympanic administration of LPT99-CD at 3 doses (50, 100 and 200 μM) was protective against CisPt-induced hearing loss, as determined by ABR. See FIGS. 5A and 5B. Administration of LPT99 attenuated the ABR threshold shift induced by CisPt at 3 days after administration, especially for high frequencies (20, 28, or 40 kHz).

This protective effect was dose dependent, showing that the 100 μM dose had the best protection profile. In addition, LPT99-CD diminished the changes induced by CisPt administration in ABR amplitudes (indicating the number of firing neurons) and peak latencies (indicating transmission speed). LPT99-CD significantly reduced the expression of p53, compared with the non-prevented cochlea.

Administration of CisPt-induced kidney injury molecule-1 (Kim-1) expression in the rat cochlea (Mukherjea, et al., Neuroscience 2006, 139(2), 8), with Kim-1 considered a marker of ototoxicity. In the tested model, it was found that Kim-1 expression decreased with LPT99-CD prevention.

Intra-tympanic administration of LPT99 solution at 2 doses (63 μg/mL [100 μM] and 300 μg/mL [478 μM]) was also protective against CisPt-induced hearing loss. At 3 days after CisPt administration, ABR thresholds had significantly increased, and DPOAE amplitudes had significantly decreased. A massive outer hair cell (OHC) loss was seen in the medial-basal parts of the cochlea, as determined by cytocochleogram analysis. The CisPt-induced increase of ABR threshold, decrease of DPOAE amplitudes, 7 and OHC cell loss were significantly prevented by IT administration of LPT99 solution, at both (63 and 300 μg/mL) doses. These results shown in FIG. 4 demonstrated significant protective effects of LPT99 solution on auditory function.

Example 6: Safety Pharmacology

Materials and Methods

In a study conducted in female Wistar rats, plasma concentrations of LPT99 were evaluated at 1 hour and 2, 4, 7, and 14 days after IT administration of a single 50 μL dose of 50, 100, or 200 μM LPT99 formulated in a 5% HPβ-cyclodextrin ("CD") vehicle (LPT99-CD).

A functional observation battery was conducted with LPT99 administered via IP (intraperitoneal) injection in Sprague-Dawley rats. The study was preceded by a non-GLP maximum tolerated dose (MTD) toxicity study, via the same administration and test system, which determined the MTD of LTP99 to be 1000 mg/kg. LPT99 was suspended in vehicle [0.5% w/v methylcellulose and 0.1% v/v TWEEN®80 in Milli-Q water] and administered intraperitoneally to Sprague-Dawley rats as a single dose at the doses of 100 (low—G2/G2TK), 300 (mid—G3/G3TK), and 750 (high—G4/G4TK) mg/kg body weight. The rats in vehicle control groups (G1/G1TK) received the vehicle alone. The dose volume administered was at an equivolume of 10 mL/kg body weight for all groups.

The potential cardiotoxicity of LPT99 was investigated in an assay using the hERG-CHO cells transfected with the automated patch clamp assay.

Results

Plasma LPT99 concentrations were below the lower limit of quantitation (BLLQ, 2 ng/mL 3.2 nM]) at all evaluated time points. A plasma concentration of 3.2 nM LPT99 corresponded to 0.006%, 0.003%, and 0.0016%, respectively, of the administered 50, 100, and 200 μM doses.

These bioavailability values are similar to those described for other drugs formulated in POLOXAMER® gels and administered IT (Honeder, et al., Audiol. Neurootol. 2014, 19(3), 193-202; Wang, et al., Audiol. Neurootol. 2011, 16(4), 233-41; Yang, et al., Sci. Transl. Med. 2016, 8(356), 356ra120). Assuming a maximum clinical dose of 200 μg LPT99 and an average human plasma volume of 2400 mL (for an average 60-kg individual [typical blood plasma volume in males is ~39 mL/kg of body weight, and in females ~40 mL/kg]). If 100% of the IT dose were 100% bioavailable, the plasma LPT99 concentration would be 0.066 μM, below the $IC_{50}$ (5.2±1.6 μM.

The neurological parameters were unaffected by the prevention at 100 mg/kg dose on Day 1. At 300 and 750 mg/kg/day, test item-related lower motor activity scores were observed in both sexes on day 1 and reversible by Day 15 and hence considered non-adverse effects.

The $IC_{50}$ of LPT99 was $3.4 \times 10^{-6}$ M. LTP99 was not detectable in plasma after IT administration, and the LPT99 detection limit of the analytical method was 3.2 nM; thus, the safety margin was >1063.

An in vitro experiment evaluating the effects of LPT99 on ion channels, including hERG potassium channels, in CHO and HEK 293 cells, LPT99 had a low torsadogenic risk. Torsadogenic refers to the development of torsade de Pointes (TdP) arrythimias.

Example 7: Pharmacokinetics and Product Metabolism in Animals

The routes for drug entry into the inner ear include the systemic circulation and the round window membrane (RWM), which connects the middle and inner ears (El Kechai, et al., Int. J. Pharm. 2015, 494(1), 19). In the case of an apoptosis inhibitor, avoiding the systemic route is of crucial importance, as this prevents any interaction with CisPt antineoplastic activity outside the cochlea. Intra-tympanic LPT99 administration is an efficient and less toxic alternative route to systemic delivery.

As described above and shown in FIG. 4, after IT administration to rats, LPT99 distributed to cochlea in a dose-dependent manner. No distribution to the contralateral cochleae or plasma was observed, which suggests that LPT99 distributes locally to the administered cochlea.

Cochleae were harvested and rinsed at several timepoints after intratympanic injection of drug product. Drug concentration (y axis) in cochlear homogenates is expressed as nanograms LPT99 per gram of cochlear homogenate.

(i) Absorption

LPT99 cochlear distribution after IT administration was studied in rats. LPT99-CD (50, 100, or 200 μM) or LPT99 solution (100 and 478 μM) was administered, and plasma samples and cochleae were collected at 1, 3, and 24 hours (for LPT99-CD), or at 1 and 3 hours and 1, 3, 7, and 14 days (for LPT99 solution) post-prevention. LPT99 concentration was quantified with an ultra-performance liquid chromatography tandem mass spectrometry (UPLC-ESI/MS/MS) system.

LPT99 was detected in all cochleae at 1 and 3 hours (LPT99-CD), and at 1 and 3 hours and 1, 3, 7, and 14 days (LPT99 solution) post-prevention.

At the 50, 100, and 200 μM doses, peak mean cochlear LPT99 concentrations of 328.5, 491.3, and 611.1 ng/g cochlea, respectively, were seen at 1 hour post-prevention. At 24 hours post-prevention, the mean cochlear LPT99 concentrations had decreased to 1.8, 13.9, and 13.4 ng/g cochlea, respectively.

In contrast, LPT99 concentrations in the contralateral cochleae and plasma were BLLQ (3 ng/g and 2 ng/mL, respectively) at all time-points and doses. These results indicated that LPT99 distributed locally to the administered cochlea and confirmed the safety of IT administration, because LPT99 levels that could offset CisPt efficacy were not detected in plasma.

(ii) Distribution:

Distribution of LPT99 was investigated in cochlea and plasma after a single IT administration in rats. The inhibitor was administered at 50, 100, or 200 μM (dissolved in 5% hydroxypropyl cyclodextrin in physiological serum).

LPT99 was detected in all administered cochleae at 0.5 and 1 hour post-prevention, showing a direct correlation between product dose and concentrations in the cochleae. Contralateral cochleae and plasma presented concentrations of LPT99 that were BLLQ at all time points.

(iii) Metabolism

The metabolic profile and stability of LPT99 was characterized in human, dog, rabbit, rat, and mouse microsomal and S9 fractions, and in human cytosolic fractions.

LPT99 was extensively metabolized (>90% metabolized after 1 hour) in microsomal and S9 hepatic fractions in all tested species. Up to nine (9) metabolites were formed through phase I biotransformation pathways. The most abundant metabolites were identified as single hydroxylation, double hydroxylation, and demethylation plus double hydroxylation. The quantities of metabolites formed by both compounds in dog, rat, and mouse species showed similar patterns to that seen in humans. In the rabbit S9 fraction, the quantity of detected metabolites was less than in the human S9 fraction.

(iv) Phototoxicity

An in vitro experiment was performed in BALB/c 3T3 mouse fibroblasts to determine the phototoxic potential of LPT99 at concentrations of ≤100 μM in 3T3 L1 cells.

LPT99 was not cytotoxic in the presence or absence of ultraviolet-visible irradiation, as indicated by the absence of a calculable photo-irritation factor. Thus, LPT99 was found to be not phototoxic.

Example 8: Single-Dose Toxicity Study—Auditory Toxicity of LPT99 after

Intra-Tympanic Administration in the Rat

The potential ototoxicity of LPT99 solution was investigated in two Non-GLP studies.

An initial experiment with LPT99 solution at concentrations of 100 μM and 200 μM showed no LPT99 ototoxicity. A follow-up experiment with LPT99 at 100 and 478 μM similarly showed no LPT99 ototoxicity.

LPT99 at 200, 400, and 797 μM showed no ototoxicity.

Example 9: Single-dose Toxicity Study of LPT99 after Intraperitoneal Administration in the Rat Acute Systemic Toxicity Model A GLP acute systemic toxicity study was conducted with LPT99 administered via IP injection in Sprague-Dawley rats. The acute systemic toxicity study was preceded by a non-GLP maximum tolerated dose (MTD) toxicity study, via the same administration and test system, which determined the MTD of LTP99 to be 1000 mg/kg.

Materials and Methods

LPT99 was suspended in vehicle [0.5% w/v methylcellulose and 0.1% v/v TWEEN® 80 in Milli-Q water] and administered intraperitoneally to Sprague-Dawley rats as a single dose at the doses of 100 (low—G2/G2TK), 300 (mid—G3/G3TK), and 750 (high—G4/G4TK) mg/kg body weight. The rats in vehicle control groups (G1/G1TK) received the vehicle alone. The dose volume administered was at an equivolume of 10 mL/kg body weight for all groups.

The main toxicity groups consist of 15 rats/sex/group in G1 and G4 groups and 10 rats/sex/group in G2 and G3 groups. The toxicokinetic groups consisted of 6 males and 6 female rats each for the prevention groups, whereas the vehicle control group had 3 male and 3 female rats.

Results

Findings from this study showed that LPT99 administration via IP injection was generally safe and well tolerated. There were no clinical signs observed in all the tested dose groups. No mortality was observed.

Toxicokinetic assessment indicated that the time to reach peak plasma concentrations ($T_{max}$) of LPT99 was observed at 24 h (except 2 h and 8 h in male and female at 100 mg/kg/day dose level) and plasma concentrations were quantifiable till 24 h at all the tested dose levels in both genders. More than dose proportional increase in peak plasma concentration ($C_{max}$) and exposure ($AUC_{last}$) was observed from 100 mg/kg/day to 750 mg/kg/day in male and approximate dose proportional increase observed in female from 100 to 750 mg/kg/day dose levels. Gender related differences were observed. Females showed approximately 1.5-5.5 fold higher exposure at all tested dose levels.

The neurological parameters were unaffected by the prevention at 100 mg/kg dose on Day 1. At 300 and 750 mg/kg/day, test item-related lower motor activity scores were observed in both sexes on day 1 and reversible by Day 15 and hence considered non-adverse effects.

At 750 mg/kg, body weights or body weight gains were not statistically significantly lower during first 7 days after injection in both sex. However, there was tendency to gains in body weights from Day 4 till the end of life, indicating reversal of the test item-related effects. At 750 mg/kg, statistically significant reduction in the food consumption was observed in males (during days 1-7) and females (during days 1-4) when compared to the control group.

LPT99 induced changes on Day 2 indicated increased neutrophil count in all prevented groups and at 750 mg/kg, this increase was also associated with increased lymphocyte and leukocyte counts in males. This increase was attributed to the acute inflammatory response around the injected material and this change did not show any microscopic correlates in hemopoietic organs.

LPT99 induced changes on Day 15 included a minimal increase in neutrophil count noted in 750 mg/kg dose group males. This increase in cell count did not show microscopic correlates in hemopoietic organs. The coagulation parameters were not affected by test item administration on both Days 2 and 15. There were no test item related changes in clinical chemistry parameters in males. In females, an increase in triglyceride concentration (60% to 147%) was noted in all prevented groups on Day 2. This change was considered as a test item related transient finding as this finding was not present on Day 15. The urinalysis parameters were unaffected by test item administration on both Days 2 and 15.

The terminal fasting body weights were not affected by test item administration at both the intervals (Day 2 and 15). On Day 2, an increase in liver weight was noted in males and females at 300 and 750 mg/kg dose groups. This increased weight was associated with the microscopic finding of hepatocellular hypertrophy and considered as an adaptive metabolic change to test item administration. An increase in epididymides weight was present at 750 mg/kg dose group males. This weight increase was attributed to the test material deposit in the epididymal fat as well as on the capsule.

Results on Day 2 indicated test material was deposited in the abdominal cavity (mesentery) which was observed over the surface of different abdominal/pelvic cavity organs namely liver, pancreas, kidneys, adipose tissue, epididymal fat and capsule, testes, seminal vesicles and coagulating gland, different intestinal segments and abdominal muscle. The grossly observed white foci/material were microscopically confirmed as the eosinophilic material surrounded by cell debris and inflammatory cells consisting mainly of neutrophils. Mediastinal lymph node white discoloration was present in all test item injected groups and microscopically necrosis/inflammation of lymph node was noted with presence of eosinophilic injected material. This could be consequent to the peritoneal space lymphatic drainage via thoracic duct to mediastinal lymph nodes.

On Day 15, as observed on Day 2, white discoloration/foci were noted in all the abdominal organs, diaphragm and mediastinal lymph nodes. However, the distribution was limited when compared to the gross lesions noted on Day 2. The microscopic morphology of these white foci also differed from Day 2. The volume of eosinophilic material was less and was surrounded predominantly by macrophages and mononuclear cells with decreased neutrophil population indicating a chronic inflammatory response.

In mediastinal lymph nodes, increased number of foamy macrophages were present without displacement of lymphoid tissue with the injected material.

At both the intervals (Day 2 and Day 15), the inflammatory response was restricted to the mesentery and surface of the visceral organs in abdominal cavity and the parenchyma was not affected. On Day 15, the reduction/absence of cell debris and lower volume of injected material on the surface of visceral organs and absence of necrosis in mediastinal lymph nodes indicate a tendency for recovery in inflammatory process.

These results demonstrate LPT99 administered via IP injection in Sprague-Dawley rats was generally safe and well tolerated at the doses used in this study. There were no clinical signs observed in all tested dose groups and no mortality was observed. Drug related changes were generally attributed to the acute inflammatory response around the injected material and were reversible.

Example 10: Genotoxicity

LPT99 showed no evidence of genetic toxicity in a GLP in vitro bacterial reverse mutation assay (Ames test).

Furthermore, in the in vitro Chinese hamster ovary (CHO) cell aberration assay, LPT99 did not induce structural aberrations in cultured mammalian cells, in the presence or absence of S9 metabolism.

The one major impurity in the active pharmaceutical ingredient, LPT102 was evaluated by quantitative structure-activity relationship ((Q)SAR) using the Derek Nexus and Leadscope Model Applier systems and identified as "inactive" for bacterial mutagenicity (SP21-17-FR).

Example 11: Physical and Chemical Stability

The aqueous solubility of LPT99 at 2.4 micromolar (uM) and in 14.7 wt/wt % LPT99 is soluble at to at least 797 micromolar (a 332-fold increase in drug solubility). It was tested for physical and chemical stability.

Physical Stability Studies:

Vials of the drug product were stored at either room temperature or 4° C. for a period greater than three months.

For vials stored at 4 C, LPT99 precipitated after a period of approximately 2 months, as evidenced by cloudy solution or solid drug sediment. However, for vials stored at room temperature, solutions remained clear with no evidence of drug precipitation.

To test the LPT99 concentration in vials, the liquid drug product was filtered through sterile 0.2 micron filters.

For vials stored at 4 C, less than 10% of the original drug concentration remained in solution, compared with 100% for vials stored at room temperature. Even physical methods of attempting drug reconstitution/dissolution (cycles of vortex, ultrasound) it was not possible to re-dissolve precipitated LPT99 in vials stored at 4 C.

Viscosity of the drug product and the temperature induced phase change was unaffected by storage conditions tested up to and exceeding 3 months.

Chemical Stability Studies:

Drug product stored at both 4 C and room temperature demonstrates chemical stability up to and exceeding 3 months.

Example 12: Local Tolerance (i) Dermal Sensitization Study

A GLP-compliant dermal sensitization study was conducted with LPT99 in guinea pigs. The objective was to assess potential dermal sensitization of LPT99 using the Buehler test (Buehler, Arch Dermatol. 1965, 91, 171-7).

The test article, LPT99, was in a neutral-pH, buffered, isotonic solution containing a thermoreversible compound. The vehicle control was buffered at neutral pH and formulated as for the test article; it contained POLOXAMER® 407, disodium phosphate dodecahydrate hydrogen, sodium dihydrogen phosphate dihydrate, sodium chloride, and water for injection.

(ii) Range-Finding Pilot Sub-Study

In the range-finding pilot substudy, 4 guinea pigs (2 males and 2 females; Charles River, Stone Ridge, N.Y.) were dosed. Guinea pigs were dosed topically in the left or right shaved scapula area with 50 µl of 1 of the 3 test article concentrations (200, 400, or 797 µM), or the vehicle control, to determine the highest nonirritating concentration that was well tolerated and that caused only mild-to-moderate irritation (i.e., a modified Draize Score of 1-2, described below) for the induction exposures. The modified Draize Score indicated separate assessments of the erythema and edema exhibited by each animal on a scale of Grade 0 to 4 for erythema and Grade 0 to 3 for edema.

No erythema or edema (both had Draize scores of 0) was observed for any of the tested LPT99 concentrations. Therefore, the highest LPT99 concentration 797 µM, was used for the induction and challenge exposure in the main study, because it was the highest nonirritating concentration used in the range-finding pilot substudy.

(iii) Dermal Sensitization Main Study

The main study consisted of 2 groups of 20 or 10 guinea pigs. Group 1 was 10 male and 10 female guinea pigs dosed with the highest concentration of LPT99, 797 µM, that was used in the dose range-finding substudy (Group 1). Group 2 was 5 male and 5 female animals that were not dosed with LPT99 (Group 2) during the induction phase and served as naïve controls; Group 2 was challenged with LPT99 on Day 28. LPT99 was topically administered to the skin in the shaved scapula area in a volume of 50 µL on Study Days 0, 7, and 14 (induction doses), and on Day 28 (challenge dose). These observations and measurements were performed: Clinical observations (daily), Body weights (weekly), Draize scoring (24 and 48 hours after bandage removal on Days 29 and 30), Primary Dermal Irritation Index (PDII) scoring of extent of irritation according to the scale in. The PDII (post-challenge) was calculated for the test article or vehicle by dividing the sum of the Total Irritation Score by the number of observations (e.g., 3 days×6 animals=18 (number of observations).

TABLE 5

Primary Dermal Irritation Index Scale

| Primary Dermal Irritation Value | Irritant Category |
|---|---|
| 0 | nonirritant |
| >0.0 to 0.5 | negligible irritant |
| >0.5 to 2.0 | mild irritant |
| >2.0 to 5.0 | moderate irritant |
| >5.0 to 7.0 | severe irritant |

No Draize scores were >0 at 24 or 48 hours after the challenge dose. The PDII score was 0, indicating that LPT99 was a nonirritant. No test-article-related changes were seen in mortality, clinical observations, body weights, or Draize scores.

Overall, topical dermal administration of 3 weekly induction doses and 1 challenge dose of 797 µM LPT99 was associated with no prevention-related effects. Based on the PDII score of 0, it was concluded that LPT99 was a nonirritant in this study.

Example 13: Ototoxicity Study of LPT99 in Rats after Single IT Administration

A GLP-compliant auditory safety study of LPT99 solution was performed in rats after acute (single-dose) IT administration.

Materials and Methods

The study consisted of 10 groups of rats: 6 groups for toxicology (Groups 1 to 6, 20 males and 20 females per group), and 4 groups for toxicokinetics (Groups 7 to 10, 6 males and 6 females per group). A single bilateral TT administration (30 µL per ear) was performed on Day 0 with vehicle (Groups 1 and 10), 200 µM LPT99 (Groups 2 and 7), 400 µM LPT99 (Groups 3 and 8), 797 µM LPT99 (Groups 4 and 9); 400 mg/mL gentamicin (Group 5); and 0.9% Sodium Chloride, USP (Group 6).

All animals were assessed weekly for body weights and qualitative food consumption. In addition, otoscopic evaluation of the dosing sites (tympanic membrane, Groups 1 to 6) and ABR testing for hearing function were performed at predosing; and on Days 1, 7, and/or 14. Animals in the toxicology groups (Groups 1 to 6) were sacrificed on Day 1 (10 males and 10 females per group) and Day 14 (the remaining 10 males and 10 females per group). At necropsy, terminal blood samples were tested for hematology, serum chemistry, and coagulation parameters. Gross observations were recorded, and selected organs were weighed. One ear per animal in Groups 1 to 5 was collected and processed for cytocochleogram assessment.

Results

In this 14-day study, there were no LPT99- or gentamicin-related mortalities, clinical abnormalities, body weight changes, food intake abnormalities, or changes in clinical pathologies (hematology, serum chemistry, or coagulation). Otoscopic examination of the tympanic membranes (i.e., the study drug administration sites) revealed no statistically significant changes in erythema, edema, or wounds in the LPT99-prevented (200, 400, or 797 µM) groups compared with the vehicle control group on Days 1, 7, or 14. Gentamicin-related increases in otoscopic scores were seen on Days 1 (males had increased erythema and wound scores; females had increased wound scores) and 7 (females had increased erythema and edema scores). However, all otoscopic score increases had disappeared by Day 14.

Organ weight assessments at Day −1 or −14 necropsies revealed no statistically significant changes in absolute, weight-normalized, or brain-weight-normalized organ weights in any LPT99 group (dosed at 200, 400, or 797 µM); or in the gentamicin group compared with the respective controls on Day 1 or 14, with the exceptions described below.

On Day 1, the male rats in the middle dose group (400 µM) showed statistically significant ($p \leq 0.05$) increases in weight-normalized liver weights compared with the vehicle controls. The increases appeared mild, with no correlation to the prevention doses; thus, the increases were considered toxicologically insignificant. On Day 14, males in the gentamicin control group had statistically significant ($p \leq 0.05$) increased weight-normalized heart weights compared with the saline controls.

Auditory brainstem response tests showed no reliable evidence of test-article-related hearing loss on Day 1 or 14. No statistically significant changes were seen in ABRs in the gentamicin group compared with the vehicle control group on Day 1 or 14, although a trend of hearing loss was observed in the gentamicin group on Day 1. Cytocochleogram analyses in cochlear samples collected at Days 1 and −14 necropsies showed no reliable evidence of test-article-related hair cell loss, except for one sample from a male in Group 4 (high dose group) sacrificed on Day 14; it is unclear whether this finding in one animal (1/20) was test-article related, since this animal exhibited no ABR alteration.

Taken together, a single IT dose of LPT99 at 200, 400, or 797 µM, administered in a volume of 30 µL per ear, was generally well tolerated.

The potential ototoxicity of LPT99 solution had been previously investigated in several non-GLP studies. An initial experiment with LPT99 solution in cyclodextrin at concentrations of 100 or 200 µM showed that LPT99, administered IT, did not produce a statistically significant increase in the thresholds in response to click or pure tones in the studied frequencies (8 to 40 kHz), or in functional parameters, including latencies and amplitudes of peaks ABR at Day 3 postprevention. In two additional non-GLP studies, IT administration of LPT99 solution in hydrogel (at 100, 300, 478, or 797 µM) did not produce a statistically significant increase in the thresholds in response to click or pure tones in the studied frequencies (8 to 40 kHz) at Days 3, 7, or 14 postprevention.

Summary of Examples

In vitro and in vivo experiments with LPT99 demonstrate that LPT99 as an Apaf-1 inhibitor is capable of inducing a cytoprotective effect via inhibition of caspase activation.

Upon IT administration, LPT99 distributes locally to the cochlea and is not detected systemically and not considered to have systemic effects.

The in vivo efficacy of LPT99, tested in a rat model of CisPt-induced hearing loss, demonstrated that LPT99 administration has protective effects against CisPt-induced hearing loss.

The potential cardiotoxicity of LPT99-mediated effects on ion channels, including hERG potassium channels in CHO and human embryonic kidney (HEK) 293 cells, indicated LPT99 had a low cardiotoxic risk.

The neurological parameters in the acute toxicology study were unaffected by the prevention with LPT99 at the doses up to 750 mg/kg evaluated in the study.

LPT99 showed no evidence of genetic toxicity in the Ames test and is not considered to induce structural aberrations in cultured mammalian cells. The only impurity detected in LPT99 DS above ICH reporting thresholds (LPT102) is also considered non-mutagenic.

Topical dermal administration of LPT99 resulted in no prevention-related effects and was considered a nonirritant.

The potential ototoxicity of LPT99 administration was investigated and was generally well tolerated. Furthermore, LPT99 was found to not be phototoxic.

LPT99 administered via IP injection in Sprague-Dawley rats was generally safe and well tolerated at the doses up to 750 mg/kg evaluated in the study. There were no clinical signs observed in all the tested dose groups and no mortality was observed. Drug related changes were generally attributed to the acute inflammatory response around the injection site and were reversible.

The formulations were chemically and structurally stable for prolonged storage at room temperature.

We claim:

1. A sustained release formulation delivering an effective amount of an apoptotic inhibitory agent for prevention or treatment of a condition, disease or disorder resulting in death of otic cells, the formulation comprising a solution of the apoptotic inhibitory agent in a non-ionic, amphiphilic polymer enhancing solubility of the apoptotic inhibitory agent at least about 100-fold compared to a corresponding formulation lacking the polymer or to water, and transitioning from a liquid state at room temperature which can be injected through a 23 gauge needle to a gel state at body temperature, wherein the apoptosis inhibitory agent is a compound of Formula I or a pharmaceutically acceptable salt thereof:

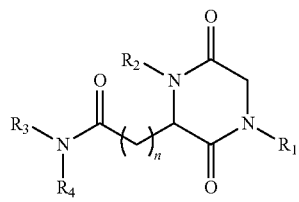

Formula I wherein:
$R_1$ and $R_2$ are independently hydrogen, $C_{1-5}$ alkyl, $C_{2-5}$ alkenyl, $(CH_2)_{0-3}$-cycloalkyl, $-(CH_2)_{1-3}$-heterocycle, $-(CH_2)_{0-3}$-aryl, $-(CH_2)_{0-3}$-heteroaryl, $-(CH_2)_{1-2}-CH(aryl)_2$, $-(CH_2)_{1-2}-CH(aryl)(heteroaryl)$, or $-(CH_2)_{1-2}-CH(heteroaryl)_2$;

$R_3$ is selected from hydrogen, $C_{1-5}$ alkyl, $C_{2-5}$ alkenyl, $(CH_2)_{0-3}$-cycloalkyl, $-(CH_2)_{1-3}$-heterocycle, $-(CH_2)_{1-3}$-aryl, $-(CH_2)_{1-3}$-heteroaryl, $-(CH_2)_{1-3}-CONR_5R_6$, $-(CH_2)_{1-2}-CH(aryl)_2$, $-(CH_2)_{1-2}-CH(aryl)(heteroaryl)$, and $-(CH_2)_{1-2}-CH(heteroaryl)_2$;

$R_4$ is hydrogen, $-C_{1-5}$ alkyl, $-(CHR_7)_{1-3}-CO-NR_5R_6$, $-(CHR_7)_{1-3}-CO-OR_5$, $-(CH_2)_{1-3}-NR_5R_6$, $-(CH_2)_{1-3}-CO[NCHR_7CO]_mNH_2$, $-(CH_2)_{1-3}-CO[NCHR_7CO]_mOR_5$;

n is 1 or 2; m is 1, 2, or 3;

$R_5$ and $R_6$ are independently selected from hydrogen, $-C_{1-5}$ alkyl, or $-(CH_2)_{0-3}$-aryl;

each $R_7$ is independently hydrogen, $-C_{1-5}$ alkyl, $-(CH_2)_{1-3}$-aryl, or $-(CH_2)_{1-3}$-heteroaryl;

wherein the $C_{1-5}$ alkyl, $C_{2-5}$ alkenyl, cycloalkyl and heterocycle groups are optionally substituted with one or more substituents selected independently from halogen, $OR_5$, $OCF_3$, SH, $SR_5$, $NR_5R_6$, $NHCOR_5$, COOH, $COOR_5$, $OCOR_5$, aryl, and heteroaryl;

wherein the aryl and heteroaryl groups are optionally substituted with one or more substituents selected independently from halogen, $CF_3$, $OR_5$, $OCF_3$, SH, $SR_5$, $NH_2$, $NHCOR_5$, $NO_2$, CN, $COR_5$, $COOR_5$, $OCOR_5$, $CONR_5R_6$, $-(CH_2)_{0-3}NR_5R_6$, $SO_2NH_2$, $NHSO_2CH_3$, $C_{1-5}$ alkyl, aryl and heteroaryl;

wherein the heterocycle and heteroaryl groups are optionally substituted on a secondary nitrogen atom with $C_{1-5}$ alkyl, cycloalkyl, or $-(CH_2)_{0-3}$-aryl; and on the condition that (i) when $R_2$ is 2-(4-fluorophenyl)ethyl, $R_4$ is $-CH_2-CO-NH_2$ and n is 1; (ii) if $R_1$ is 2-(4-fluorophenyl)ethyl, $R_3$ is not 2-(4-methoxyphenyl)ethyl, 2-(2-pyridyl)ethyl or 2-(2,4-dichlorophenyl)ethyl; and (iii) if $R_1$ is 2-(2,4-dichlorophenyl)ethyl, $R_3$ is not 2-(4-methoxyphenyl)ethyl, or 2-(2-pyridyl)ethyl, wherein the polymer is a synthetic polymer selected from the group consisting of N-isopropylacrylamide (NiPAAM) polymers, poly(ethylene oxide)-b-poly(propylene oxide)-b-poly(ethylene oxide) (PEO-PPO-PEO), poly(ethylene glycol) (PEG)-biodegradable polyester copolymers, block copolymers of ethylene oxide and propylene oxide, and tetrafunctional block copolymer derived from sequential addition of propylene oxide and ethylene oxide to ethylenediamine, the solution having a pH between 6 and 8 and an osmolarity of at least 100 mOsmol/kg.

2. The formulation of claim 1, wherein the apoptotic inhibitory agent inhibits a protein in an apoptosis pathway.

3. The formulation of claim 2 wherein the apoptotic inhibitory agent inhibits apoptotic protease activating factor-1 (Apaf-1) or reduces cyt-c release.

4. The formulation of claim 1, wherein the condition, disease or disorder is hearing loss associated with exposure to ototoxic agents exposure to loud noise, aging, Meniere's disease, sudden sensorineural hearing loss, autoimmune inner ear disease or a combination thereof.

5. The formulation of claim 1 wherein the polymer enhances solubility of the apoptotic inhibitory agent at least about 300-fold or 1000-fold, compared to a corresponding formulation lacking the polymer or to water.

6. The formulation of claim 5 wherein the apoptotic inhibitory agent is stable in the formulation at room temperature for a period of at least three months.

7. The formulation of claim 1, wherein the apoptosis inhibitory agent is hydrophobic and/or a small molecule.

8. The formulation of claim 1, wherein the apoptosis inhibitory agent inhibits apoptosis of sensorineural cells from an insult that causes loss of a portion of hair cells, neurons, or stria vascularis cells or maintains the tight junctions between the cells.

9. The formulation of claim 1, wherein the apoptosis inhibitory agent contains a 1,4-piperazine-2,5-dione moiety or a pharmaceutically acceptable salt thereof.

10. The formulation of claim 1, wherein
R$_1$ and R$_2$ are independently $(CH_2)_{0-3}$-cycloalkyl, $—(CH_2)_{1-3}$-heterocycle, $—(CH_2)_{0-3}$-aryl, $—(CH_2)_{0-3}$-heteroaryl, $—(CH_2)_{1-2}—CH(aryl)_2$, $—(CH_2)_{1-2}—CH(aryl)(heteroaryl)$, or $—(CH_2)_{1-2}—CH(heteroaryl)_2$.

11. The formulation of claim 10, wherein the apoptosis inhibitory agent is a compound having the structure:

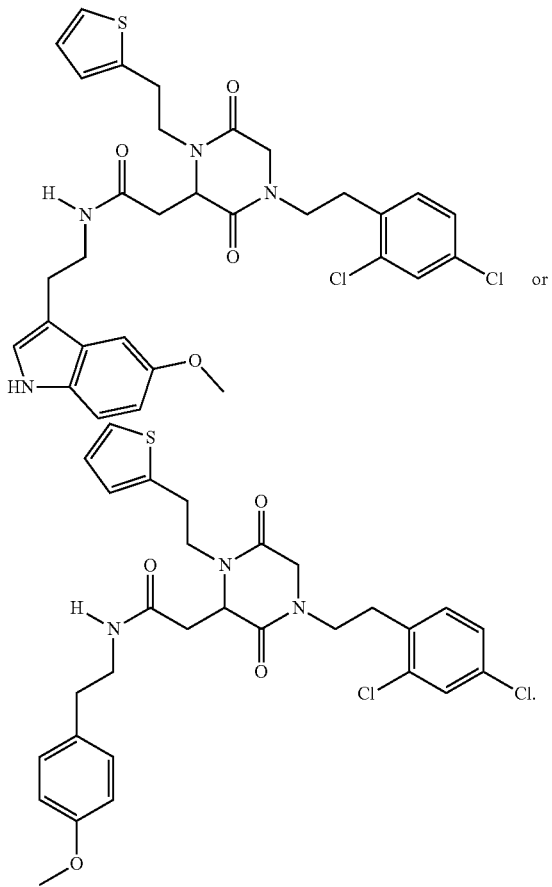

12. The formulation of claim 1, wherein the apoptosis inhibitory agent contains a 1,4-piperazine-2,5-dione moiety or a pharmaceutically acceptable salt thereof, and is present in a concentration of between about 50 µM and about 1000 µM, between about 125 and about 1500 mcg/ml, or between about 0.0031% and about 1.5% w/w in the formulation.

13. The formulation of claim 12, wherein the apoptotic inhibitory agent is 2-(4-(2,4-dichlorophenethyl)-3,6-dioxo-1-(2-(thiophen-2-yl)ethyl)piperazin-2-yl)-N-(2-(5-methoxy-1H-indol-3-yl)ethyl)acetamide.

14. The formulation of claim 1, wherein the gel state provides sustained release of the apoptosis inhibitory agent for a period of between at least about three days and 30 days.

15. The formulation of claim 12, wherein the non-ionic, amphiphilic polymer is a poly(ethylene oxide)-poly(propylene oxide) triblock copolymer having a formula A-B-A or B-A-B at a concentration of between about 10% to about 30% w/w in the formulation, wherein A is poly(ethylene oxide) and B is poly(propylene oxide).

16. The formulation of claim 1, wherein the polymer is a synthetic polymer selected from the group consisting of poly(ethylene glycol) (PEG)-biodegradable polyester copolymers.

17. The formulation of claim 1, having a pH between about 6.8 and about 7.7, and an osmolality between about 240 mOsmol/kg and about 350 mOsmol/kg.

18. The formulation of claim 17, having a pH of 7.2, and an osmolality of about 280 mOsmol/kg.

19. A method of preventing or treating a condition, disease or disorder associated with apoptosis or cell death in ear, comprising:
administering through a 23 gauge or higher needle into the inner ear of a person with or at risk of the condition, disease or disorder the sustained release formulation of claim 1 delivering an apoptotic inhibitory agent for prevention or treatment of the condition, disease or disorder.

20. A method of making the sustained release formulation of claim 1 delivering an apoptotic inhibitory agent for prevention or treatment of a condition, disease or disorder associated with apoptosis in ear, comprising:
mixing the apoptotic inhibitory agent in a formulation comprising an effective amount of the polymer to form a solution.

21. The formulation of claim 4, wherein the ototoxic agents comprise chemotherapeutics.

22. The formulation of claim 8, wherein the sensorineural cells comprise cochlear hair cells.

* * * * *